US011885757B2

(12) United States Patent
Gettemy et al.

(10) Patent No.: US 11,885,757 B2
(45) Date of Patent: Jan. 30, 2024

(54) MATERIAL PROPERTIES FROM TWO-DIMENSIONAL IMAGE

(71) Applicant: BP Corporation North America Inc., Houston, TX (US)

(72) Inventors: Glen L. Gettemy, Katy, TX (US); Nirjhor Chakraborty, Houston, TX (US); Milad Saidian, Houston, TX (US)

(73) Assignee: BP Corporation North America Inc., Houston, TX (US)

( * ) Notice: Subject to any disclaimer, the term of this patent is extended or adjusted under 35 U.S.C. 154(b) by 463 days.

(21) Appl. No.: 17/316,144

(22) Filed: May 10, 2021

(65) Prior Publication Data
US 2021/0349042 A1 Nov. 11, 2021

Related U.S. Application Data

(60) Provisional application No. 63/021,885, filed on May 8, 2020.

(51) Int. Cl.
*G01N 23/2251* (2018.01)
*G06T 7/143* (2017.01)
(Continued)

(52) U.S. Cl.
CPC ......... *G01N 23/2251* (2013.01); *G01N 33/24* (2013.01); *G06T 7/10* (2017.01);
(Continued)

(58) Field of Classification Search
CPC .............. G01N 23/2251; G01N 33/24; G01N 2223/07; G01N 2223/401;
(Continued)

(56) References Cited

U.S. PATENT DOCUMENTS

| 9,348,056 B2 * | 5/2016 | Fredrich | G06T 7/11 |
| 2008/0221800 A1 * | 9/2008 | Gladkikh | G01V 5/04 |
| | | | 702/11 |

(Continued)

FOREIGN PATENT DOCUMENTS

WO    WO-2022098645 A1 *    5/2022    ......... G01N 15/0826

OTHER PUBLICATIONS

Tahmasebi et al: "Stochastic shale permeability matching: Three-dimensional characterization and modeling", International Journal of Coal Geology, Elsevier, Amsterdam, NL; vol. 165, Aug. 29, 2016, pp. 231-242, XP029756537, ISSN: 0166-5162.
(Continued)

*Primary Examiner* — David A Vanore
(74) *Attorney, Agent, or Firm* — Conley Rose, P.C.

(57) ABSTRACT

A method for analyzing a rock sample includes segmenting a digital image volume corresponding to an image of the rock sample, to associate voxels in the digital image volume with a plurality of rock fabrics of the rock sample. The method also includes identifying a set of digital planes through the digital image volume. The set of digital planes intersects with each of the plurality of rock fabrics. The method further includes machining the rock sample to expose physical faces that correspond to the identified digital planes, performing scanning electron microscope (SEM) imaging of the physical faces to generate two-dimensional (2D) SEM images of the physical faces, and performing image processing on the SEM images to determine a material property associated with each of the rock fabrics.

18 Claims, 21 Drawing Sheets

(51) Int. Cl.
　　*G06T 7/11*　　　(2017.01)
　　*G06T 7/174*　　(2017.01)
　　*G01N 33/24*　　(2006.01)
　　*G06T 7/10*　　　(2017.01)
　　*G06T 7/00*　　　(2017.01)
　　*G06T 17/00*　　(2006.01)

(52) U.S. Cl.
　　CPC ............... *G06T 7/11* (2017.01); *G06T 7/143* (2017.01); *G06T 7/174* (2017.01); *G06T 7/97* (2017.01); *G06T 17/00* (2013.01); *G01N 2223/07* (2013.01); *G01N 2223/401* (2013.01); *G01N 2223/418* (2013.01); *G01N 2223/507* (2013.01); *G01N 2223/616* (2013.01); *G06T 2207/10024* (2013.01); *G06T 2207/10061* (2013.01)

(58) Field of Classification Search
　　CPC ....... G01N 2223/418; G01N 2223/507; G01N 2223/616; G06T 7/10; G06T 7/11; G06T 7/143; G06T 7/174; G06T 7/97; G06T 17/00; G06T 2207/10024; G06T 2207/10061; G06T 2207/10081; G06T 2207/30108; G06T 2207/30181; G06T 7/136; G06T 7/0004

See application file for complete search history.

(56) References Cited

U.S. PATENT DOCUMENTS

| | | | | |
|---|---|---|---|---|
| 2016/0139291 | A1* | 5/2016 | Saidian | G01N 24/081 |
| | | | | 324/303 |
| 2016/0320323 | A1* | 11/2016 | Saidian | G01R 33/448 |
| 2021/0349070 | A1* | 11/2021 | Gettemy | G06T 7/0004 |
| 2022/0082517 | A1* | 3/2022 | Song | G01N 33/241 |
| 2022/0317015 | A1* | 10/2022 | Sun | G01N 15/088 |
| 2023/0288606 | A1* | 9/2023 | Zapata Arboleda | .............. |
| | | | | G01V 99/005 |
| | | | | 703/6 |

OTHER PUBLICATIONS

Mehmani Ayaz et al: "Pore-scale modeling of carbonates", Marine and Petroleum Geology, Elsevier, Amsterdam, NL; vol. 114, Nov. 20, 2019, XP086013706, ISSN: 0264-8172.

Tahmasebi et al: "Three-Dimensional Stochastic Characterization of Shale SEM Images", Transport in Porous Media, Reidel, Dordrecht, NL; vol. 110, No. 3; Sep. 4, 2015, pp. 521-531, XP035577540, ISSN: 0169-3913.

Ji et al: "A multiscale reconstructing method for shale based on SEM image and experiment data", Journal of Petroleum Science and Engineering, vol. 179, Aug. 31, 2019, pp. 586-599, XP085704319, ISSN: 0920-4105.

International Search Report and Written Opinion dated Aug. 23, 2021, for Application No. PCT/US2021/031619.

Tahmasebi, Pejman et al., "MS-CCSIM: Accererating pattern-based geostatistical simulation of categorical variables using a multi-scale search in Fourier space," Computers & Geosciences 67 (2014) 75-88 (14 pgs).

\* cited by examiner

MATERIAL PROPERTIES FROM TWO-DIMENSIONAL IMAGE

CROSS-REFERENCE TO RELATED APPLICATIONS

The present application claims benefit of U.S. provisional patent application No. 63/021,885 filed May 8, 2020, and entitled "Material Properties from Two-Dimensional Image" which is incorporated herein in its entirety for all purposes.

BACKGROUND

In hydrocarbon production, obtaining accurate subsurface estimates of petrophysical properties of the rock formations is important for the assessment of hydrocarbon volumes contained in the rock formations and for formulating a strategy for extracting the hydrocarbons from the rock formation. Traditionally, samples of the rock formation, such as from core samples or drilling cuttings, are subjected to physical laboratory tests to measure petrophysical properties such as permeability, porosity, formation factor, elastic moduli, and the like. Some of these measurements require long time periods, extending over several months in some cases, depending on the nature of the rock itself. The equipment used to make these measurements can also be quite costly.

Due to the cost and time required to directly measure petrophysical properties, the technique of "direct numerical simulation" can be applied to efficiently estimate physical properties, such as porosity, absolute permeability, relative permeability, formation factor, elastic moduli, and the like of rock samples, including samples from difficult rock types such as tight gas sands or carbonates. According to this approach, a three-dimensional tomographic image of the rock sample is obtained, for example by way of a computer tomographic (CT) scan. Voxels in the three-dimensional image volume are "segmented" (e.g., by "thresholding" their brightness values or by another approach) to distinguish rock matrix from void space. Direct numerical simulation of fluid flow or other physical behavior such as elasticity or electrical conductivity is then performed, from which porosity, permeability (absolute and/or relative), elastic properties, electrical properties, and the like can be derived. A variety of numerical methods may be applied to solve or approximate the physical equations simulating the appropriate behavior. These methods include the Lattice-Boltzmann, finite element, finite difference, finite volume numerical methods and the like.

SUMMARY

In accordance with at least one example of the disclosure, a method for analyzing a rock sample includes segmenting a digital image volume corresponding to an image of the rock sample, to associate voxels in the digital image volume with a plurality of rock fabrics of the rock sample. The method also includes identifying a set of digital planes through the digital image volume. The set of digital planes intersects with each of the plurality of rock fabrics. The method further includes machining the rock sample to expose physical faces that correspond to the identified digital planes, performing scanning electron microscope (SEM) imaging of the physical faces to generate two-dimensional (2D) SEM images of the physical faces, and performing image processing on the SEM images to determine a material property associated with each of the rock fabrics.

In accordance with another example of the disclosure, a system for analyzing a rock sample includes a first imaging device configured to produce a digital image volume representative of the rock sample, a scanning electron microscope (SEM) configured to generate two-dimensional (2D) SEM images of physical faces of the rock sample, and a computing device coupled to the imaging device and SEM. The computing device includes a processor and a memory coupled to the processor. The memory is configured to store instructions that, when executed by the processor, configure the computing device to segment the digital image volume, to associate voxels in the digital image volume with a plurality of rock fabrics of the rock sample. When executed by the processor, the instructions also configure the computing device to identify a set of digital planes through the digital image volume. The set of digital planes intersects with each of the plurality of rock fabrics and corresponds to the physical faces. When executed by the processor, the instructions further configure the computing device to perform image processing on the SEM images to determine a material property associated with each of the rock fabrics.

In accordance with yet another example of the disclosure, a non-transitory, computer-readable medium is encoded with instructions that, when executed by a processor, cause the processor to segment a digital image volume corresponding to an image of a rock sample, to associate voxels in the digital image volume with a plurality of rock fabrics of the rock sample. The instructions, when executed by the processor, also cause the processor to identify a set of digital planes through the digital image volume. The set of digital planes intersects with each of the plurality of rock fabrics. The instructions, when executed by the processor, further cause the processor to receive two-dimensional (2D) scanning electron microscope (SEM) images of physical faces of the rock sample that correspond to the identified digital planes and perform image processing on the SEM images to determine a material property associated with each of the rock fabrics.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a detailed description of exemplary embodiments, reference will now be made to the accompanying drawings, which may not be drawn to scale, in which.

NOTATION AND NOMENCLATURE

Figure 1A:
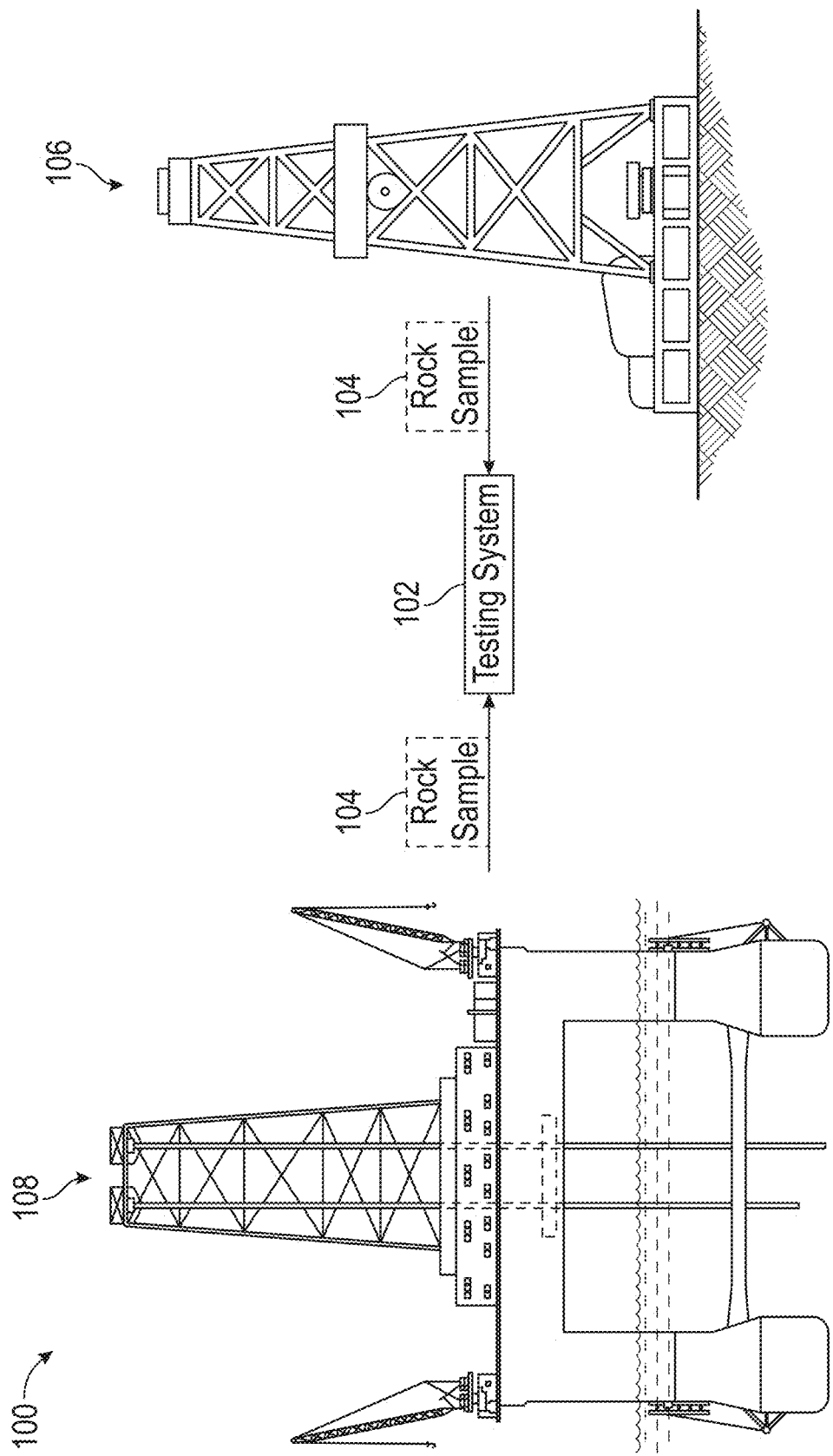
FIG. 1a is a schematic level diagram that illustrates examples of sources of rock samples for a testing system constructed and operating in accordance with principles disclosed herein.

In the following discussion and in the claims, the terms "including" and "comprising" are used in an open-ended fashion, and thus should be interpreted to mean "including, but not limited to . . . ". Any use of any form of the terms "connect", "engage", "couple", "attach", or any other term describing an interaction between elements is not meant to limit the interaction to direct interaction between the elements and may also include indirect interaction between the elements described. The term "software" includes any executable code capable of running on a processor, regardless of the media used to store the software. Thus, code stored in memory (e.g., non-volatile memory), and sometimes referred to as "embedded firmware," is included within the definition of software. The recitation "based on" is intended to mean "based at least in part on." Therefore, if X is based on Y, X may be based on Y and any number of additional factors.

DETAILED DESCRIPTION

In the drawings and description that follow, like parts are typically marked throughout the specification and drawings with the same reference numerals. The drawing figures are not necessarily to scale. Certain features of embodiments may be shown exaggerated in scale or in somewhat schematic form, and some details of conventional elements may not be shown in the interest of clarity and conciseness. The present disclosure is susceptible to embodiments of different forms. Specific embodiments are described in detail and are shown in the drawings, with the understanding that the present disclosure is to be considered an exemplification of the principles of the disclosure, and is not intended to limit the disclosure to that illustrated and described herein. It is to be fully recognized that the different teachings and components of the embodiments discussed below may be employed separately or in any suitable combination to produce desired results.

Unconventional shale reservoirs are heterogeneous in nature, and thus present complications when trying to model the behavior of such shale reservoirs. Improved understanding of how nano-microscale fabrics control fluid flow in a shale reservoir would be beneficial for optimizing or improving the production of hydrocarbons. Achieving such understanding has been difficult. Imaging a rock sample from a shale reservoir to characterize its nano-microscale fabrics, in terms of their impact on total hydrocarbon volume and fluid flow, requires high resolutions. Currently, a focused ion beam-scanning electron microscope (FIB-SEM) may provide 3D information at such resolutions. However, AB-SEM imaging of a rock sample is extremely time- and resource-intensive, and thus cannot be performed cost-effectively, and cannot be performed effectively at the scale necessary for characterization of nano-microscale fabrics of a rock sample. Further, existing attempts to leverage FIB-SEM imaging to model behavior of shale reservoirs do not describe the uncertainties of determined material properties, which is important when developing a risk profile for a well production plan. For example, FIB-SEM imaging is insufficient in this regard because the field of view for a given FIB-SEM image is limited. Additionally, physically sampling a large diversity of manifestations in a textural family is time-consuming. Further, even if a specific region of a two-dimensional SEM image was targeted to acquire statistically representative 3D AB-SEM samples, the initially-available 2D surface information is a poor indicator of what may be acquired from the underlying 3D volume.

FIG. 1a illustrates, at a high level, the acquiring of rock samples and the analysis of the rock samples according to principles disclosed herein. Embodiments of present disclosure may be especially beneficial in analyzing rock samples from sub-surface formations that are important in the production of oil and gas. As such, FIG. 1a illustrates environments 100 from which rock samples 104 to be analyzed by testing system 102 can be obtained, according to various implementations. In these illustrated examples, rock samples 104 can be obtained from terrestrial drilling system 106 or from marine (ocean, sea, lake, etc.) drilling system 108, either of which is utilized to extract resources such as hydrocarbons (oil, natural gas, etc.), water, and the like. As is fundamental in the art, optimization of oil and gas production operations is largely influenced by the structure and material properties of the rock formations into which terrestrial drilling system 106 or marine drilling system 108 is drilling or has drilled in the past.

The manner in which rock samples 104 are obtained, and the physical form of those samples, can vary widely. Examples of rock samples 104 useful in connection with embodiments disclosed herein include whole core samples, side wall core samples, outcrop samples, drill cuttings, and laboratory generated synthetic rock samples such as sand packs and cemented packs.

As illustrated in FIG. 1a, the environment 100 includes testing system 102 that is configured to analyze images 128 (FIG. 1b) of rock samples 104 in order to determine the material properties of the corresponding sub-surface rock, such properties including petrophysical properties in the context of oil and gas exploration and production.

Figure 1B:
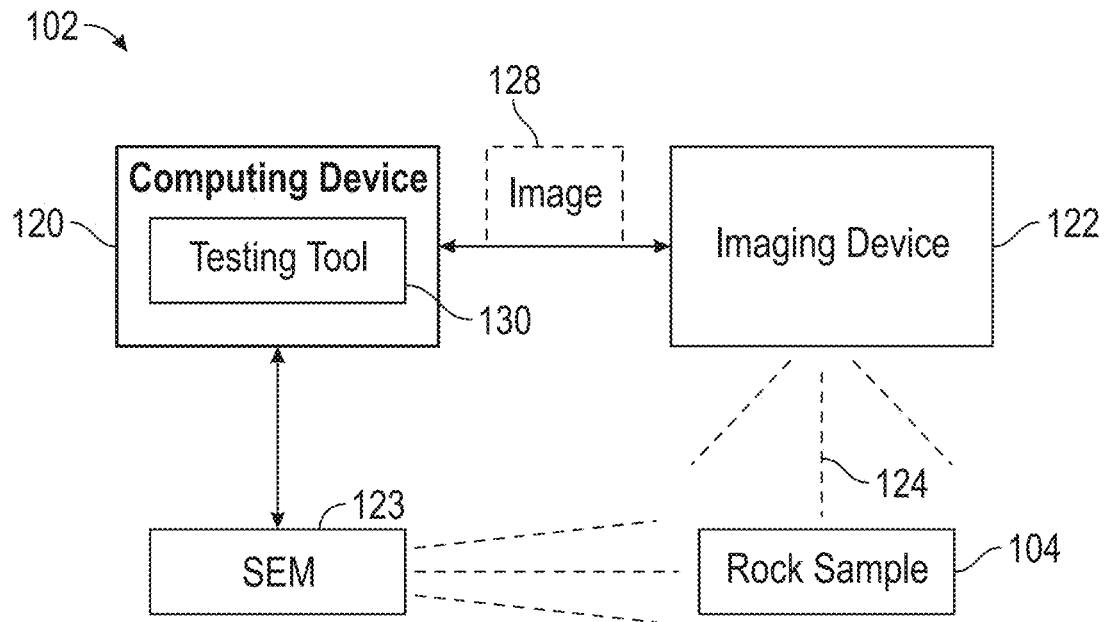
FIG. 1b shows a block diagram for a testing system for analyzing rock samples in accordance with principles disclosed herein.

FIG. 1b illustrates, in a generic fashion, the constituent components of the testing system 102 that analyzes images 128. In a general sense, testing system 102 includes imaging device 122 for obtaining 2D or 3D images, as well as other representations, of rock samples 104, such images and representations including details of the internal structure of the rock samples 104. An example of imaging device 122 is an X-ray computed tomography (CT) scanner, which, as known in the art, emits x-ray radiation 124 that interacts with an object and measures the attenuation of that x-ray radiation 124 by the object in order to generate an image of its interior structure and constituents. The particular type, construction, or other attributes of CT scanner 122 can correspond to that of any type of x-ray device, such as a micro CT scanner, capable of producing an image representative of the internal structure of rock sample 104. The imaging device 122 generates one or more images 128 of rock sample 104, and forwards those images 128 to a computing device 120.

The images 128 produced by imaging device 122 may be in the form of a three-dimensional (3D) digital image volume (i.e., a digital rock) consisting of or generated from a plurality of two-dimensional (2D) sections of rock sample 104. In this case, each image volume is partitioned into 3D regular elements called volume elements, or more commonly "voxels". In general, each voxel is a parallelepiped that may have different dimensions in the x, y, and z directions. In some examples, a voxel may also be cubic, having a side of equal length in the x, y, and z directions. Digital image volume 128 itself, on the other hand, may contain different numbers of voxels in the x, y, and z directions. Each voxel within a digital volume has an associated numeric value, or amplitude, that represents the relative material properties of the imaged sample at that location of the medium represented by the digital volume. The range of these numeric values, commonly known as the grayscale range, depends on the type of digital volume, the granularity of the values (e.g., 8-bit or 16-bit values), and the like. For example, 16-bit data values enable the voxels of an x-ray tomographic image volume to have amplitudes ranging from 0 to 65,536 with a granularity of 1.

The testing system 102 may also include a scanning electron microscope (SEM) 123 for obtaining 2D SEM images of rock samples 104. The SEM 123 is also coupled to the computing device 120, and thus the 2D SEM images produced by the SEM 123 are available to (e.g., received by) the computing device 120, which processes such 2D SEM images as described further below.

As mentioned above, imaging device 122 forwards images 128 to computing device 120, which in the example of FIG. 1b may be any type of computing device, for example, a desktop computer or workstation, a laptop computer, a server computer, a tablet computer, and the like. The SEM 123 also forwards 2D SEM images to the computing device 120. As such computing device 120 will include hardware and software components typically found in a conventional computing device. As shown in FIG. 1b, these hardware and software components of computing device 120 include a testing tool 130 that is configured to analyze images 128 to determine the petrophysical properties of rock sample 104 under one or more simulated fluid saturation conditions, including fluid saturation conditions that may be encountered by rock formations in the sub-surface. In this regard, the testing tool 130 may be implemented as software, hardware, or a combination of both, including the necessary and useful logic, instructions, routines, and algorithms for performing the functionality and processes described in further detail herein. In a general sense, testing tool 130 is configured to analyze image volume 128 of rock sample 104 to perform direct numerical simulation of the petrophysical properties under fluid saturation conditions representing subsurface conditions of rock formations, including variation degrees of saturation with multiple fluids.

Figure 1C:
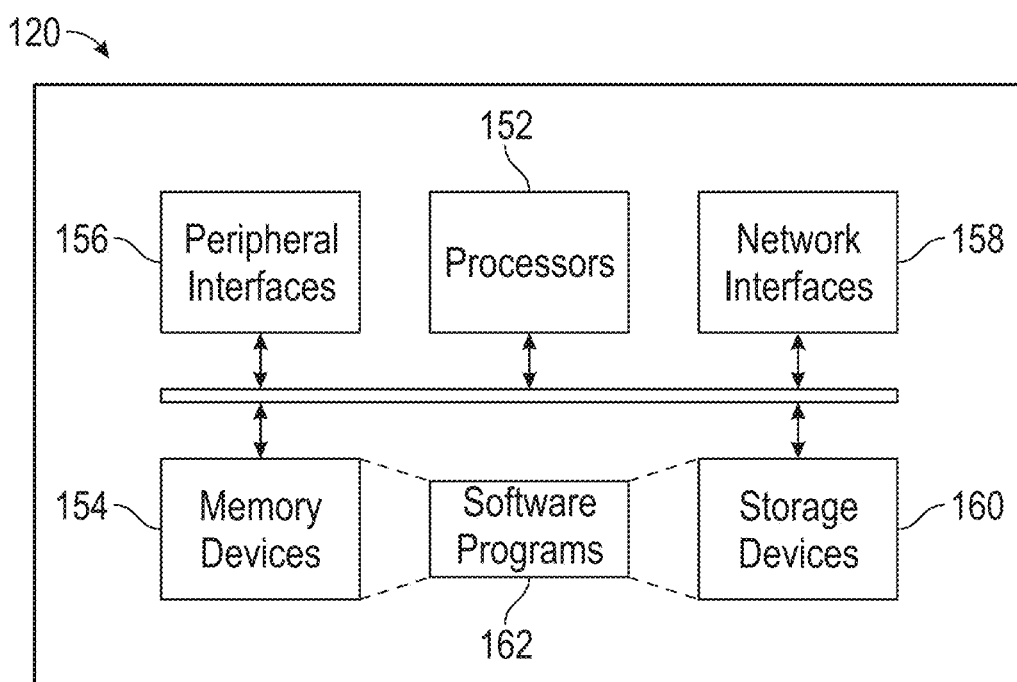
FIG. 1c shows a block diagram for a computing device suitable for use in a testing system for analyzing rock samples in accordance with principles disclosed herein.

FIG. 1c generically illustrates the architecture of computing device 120 in testing system 102 according to various embodiments. In this example architecture, computing device 120 includes one or more processors 152, which may be of varying core configurations and clock frequencies as available in the industry. The memory resources of computing device 120 for storing data and/or program instructions for execution by the one or more processors 152 include one or more memory devices 154 serving as a main memory during the operation of computing device 120, and one or more storage devices 160, for example realized as one or more of non-volatile solid-state memory, magnetic or optical disk drives, or random-access memory. One or more peripheral interfaces 156 are provided for coupling to corresponding peripheral devices such as displays, keyboards, mice, touchpads, touchscreens, printers, and the like. Network interfaces 158, which may be in the form of Ethernet adapters, wireless transceivers, serial network components, etc. are provided to facilitate communication between computing device 120 via one or more networks such as Ethernet, wireless Ethernet, Global System for Mobile Communications (GSM), Enhanced Data rates for GSM Evolution (EDGE), Universal Mobile Telecommunications System (UMTS), Worldwide Interoperability for Microwave Access (WiMAX), Long Term Evolution (LTE), and the like. In this example architecture, processors 152 are shown as coupled to components 154, 156, 158, and 160 by way of a single bus; of course, a different interconnection architecture such as multiple, dedicated, buses and the like may be incorporated within computing device 120.

While illustrated as a single computing device, computing device 120 can include several computing devices cooperating together to provide the functionality of a computing device. Likewise, while illustrated as a physical device, computing device 120 can also represent abstract computing devices such as virtual machines and "cloud" computing devices.

As shown in the example implementation of FIG. 1c, the computing device 120 includes software programs 162 including one or more operating systems, one or more application programs, and the like. According to embodiments, software programs 162 include program instructions corresponding to testing tool 130 (FIG. 1b), implemented as a standalone application program, as a program module that is part of another application or program, as the appropriate plug-ins or other software components for accessing testing tool software on a remote computer networked with computing device 120 via network interfaces 158, or in other forms and combinations of the same.

The program memory storing the executable instructions of software programs 162 corresponding to the functions of testing tool 130 may physically reside within computing device 120 or at other computing resources accessible to computing device 120, i.e. within the local memory resources of memory devices 154 and storage devices 160, or within a server or other network-accessible memory resources, or distributed among multiple locations. In any case, this program memory constitutes a non-transitory computer-readable medium that stores executable computer program instructions, according to which the operations described in this specification are carried out by computing device 120, or by a server or other computer coupled to computing device 120 via network interfaces 158 (e.g., in the form of an interactive application upon input data communicated from computing device 120, for display or output by peripherals coupled to computing device 120). The computer-executable software instructions corresponding to software programs 162 associated with testing tool 130 may have originally been stored on a removable or other non-volatile computer-readable storage medium (e.g., a DVD disk, flash memory, or the like), or downloadable as encoded information on an electromagnetic carrier signal, in the form of a software package from which the computer-executable software instructions were installed by computing device 120 in the conventional manner for software installation. It is contemplated that those skilled in the art will be readily able to implement the storage and retrieval of the applicable data, program instructions, and other information useful in connection with this embodiment, in a suitable manner for each particular application, without undue experimentation.

The particular computer instructions constituting software programs 162 associated with testing tool 130 may be in the form of one or more executable programs, or in the form of source code or higher-level code from which one or more executable programs are derived, assembled, interpreted or compiled. Any of a number of computer languages or protocols may be used, depending on the manner in which the desired operations are to be carried out. For example, these computer instructions for creating the model according to embodiments may be written in a conventional high-level language such as PYTHON, JAVA, FORTRAN, or C++, either as a conventional linear computer program or arranged for execution in an object-oriented manner. These instructions may also be embedded within a higher-level application. In any case, it is contemplated that those skilled in the art having reference to this description will be readily able to realize, without undue experimentation, embodiments in a suitable manner for the desired installations.

The particular functions of testing tool 130, including those implemented by way of software programs 162, to analyze rock samples under various saturation conditions according to embodiments, will now be described with reference to FIGS. 2A and 2B in combination with FIGS. 1a-1c.

Figure 2A:
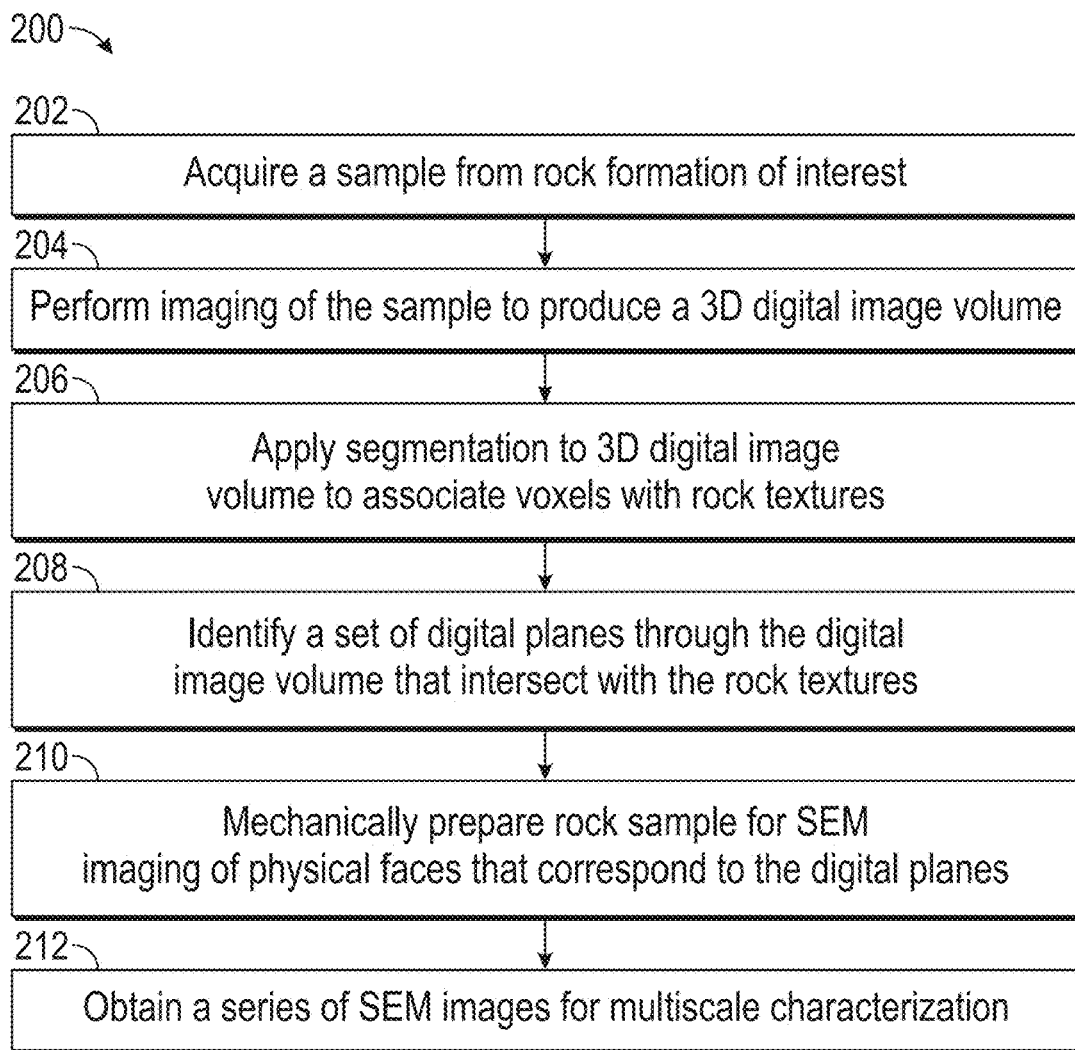
FIGS. 2A and 2B show a flow diagram for a method for analyzing rock samples in accordance with principles disclosed herein.
Figure 2B:
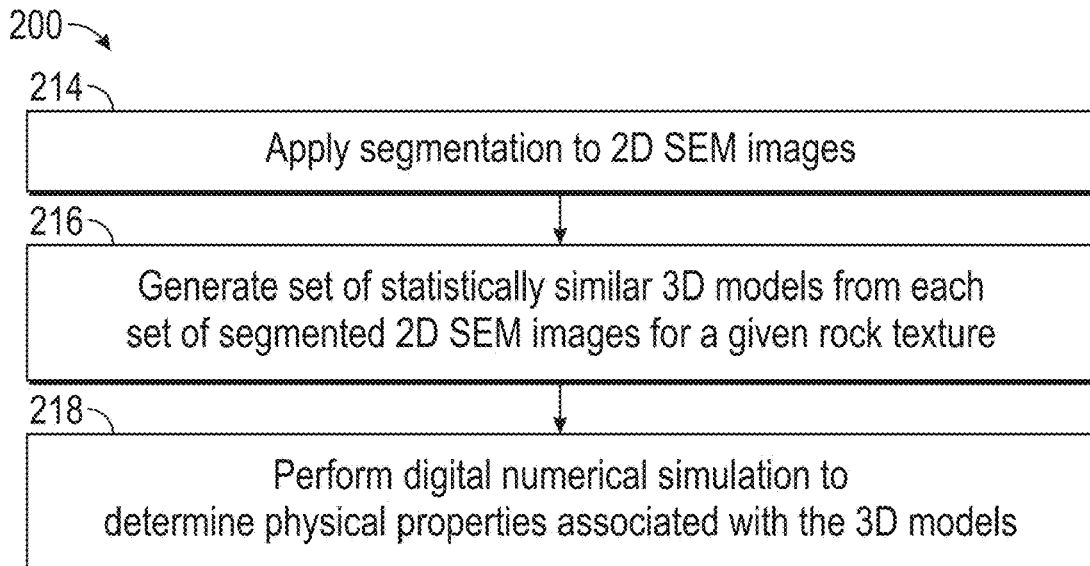

FIGS. 2A and 2B show a flow diagram for a method 200 for analyzing rock samples under various saturation conditions in accordance with principles disclosed herein. Though depicted sequentially as a matter of convenience, at least some of the actions shown can be performed in a different order and/or performed in parallel. Additionally, some embodiments may perform only some of the actions shown. In some embodiments, at least some of the operations of the method 200, as well as other operations described herein, can be implemented as instructions stored in a computer readable medium and executed by one or more processors 152.

In block 202, the testing system 102 acquires rock sample 104 to be analyzed, such as from a sub-surface rock formation obtained via terrestrial drilling system 106 or marine drilling system 108, or from other sources. The specific rock sample 104 may be prepared from a larger volume of the sub-surface rock formation, to be of a size, dimension, and configuration that may be imaged by imaging device 122 (e.g., a CT scanner), for example by drilling or cutting out a portion of the larger volume of the rock formation of interest.

In block 204, imaging device 122 in combination with computing device 120 of testing system 102 generates digital image volume 128 representative of rock sample 104, including its interior structure. For example, if the imaging device 122 is a CT scanner, then X-ray imaging of rock sample 104 is performed (i.e., emitting radiation directed at rock sample 104 and measuring the attenuation) to generate image volumes 128 of or from 2D slice images. Specific conventional techniques for acquiring and processing 3D digital image volumes 128 of rock sample 104 in block 204 include, without limitation, X-ray tomography, X-ray microtomography, X-ray nano-tomography, Focused Ion Beam Scanning Electron Microscopy, and Nuclear Magnetic Resonance Imaging. In some embodiments, the digital image volume 128 may be computationally generated rather than produced by scanning a physical specimen. In embodiments in which the digital image volume 128 is produced by scanning a rock specimen, the rock specimen may be a naturally occurring rock or a man-made porous material (e.g., a synthetic rock).

Figure 3A:
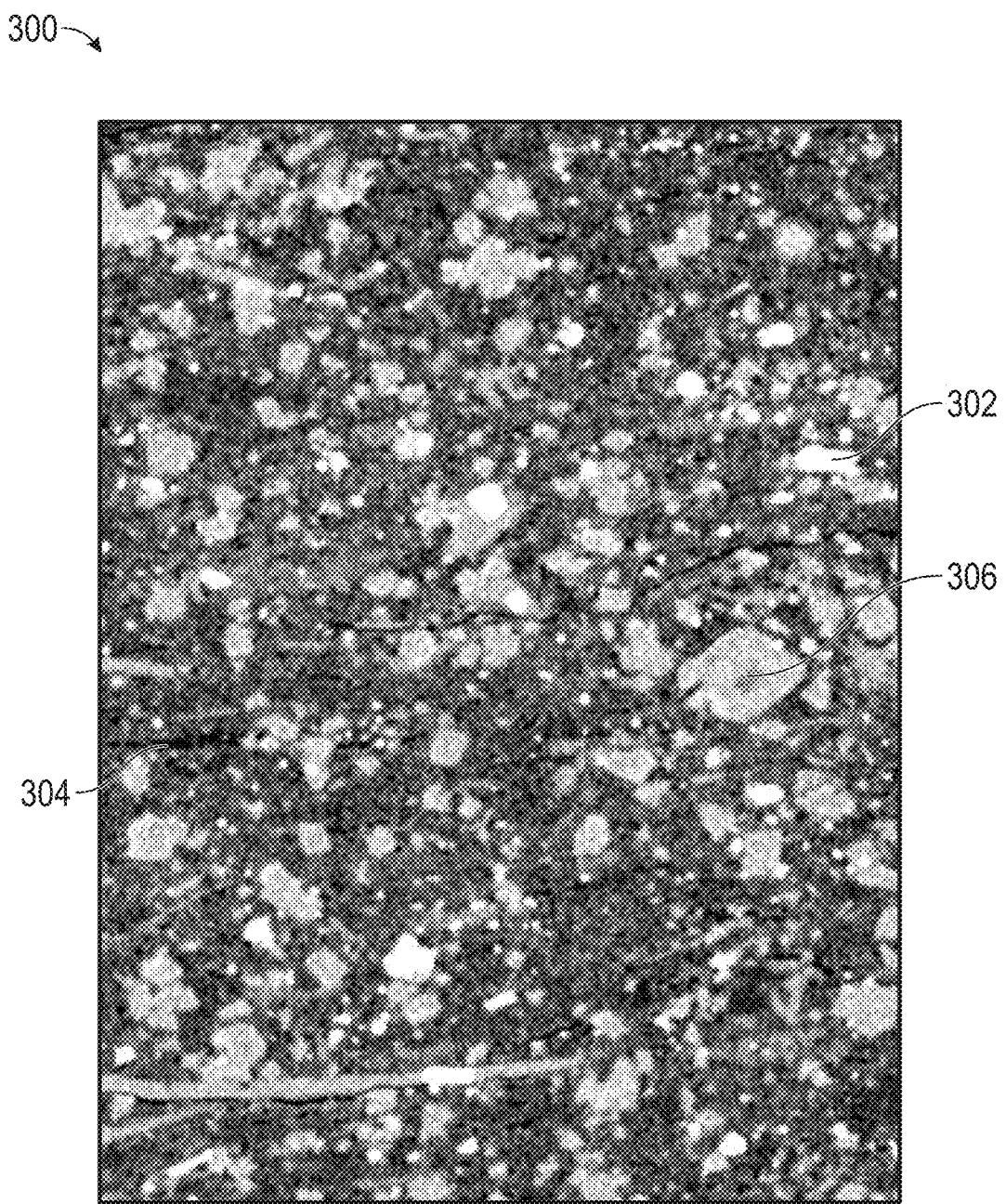
FIGS. 3a and 3b show a two-dimensional (2D) slice image of a three-dimensional (3D) image of a rock sample suitable for use with various embodiments disclosed herein.

FIG. 3a illustrates an example of one 2D slice image 300 of a 3D image of a rock sample, which shows a cross-sectional slice of the structural details of that rock sample, including the features of solid material 302, pore or void space 304, and partial solid/pore space 306. The image data at this point may be in the form of grayscale values representative of the attenuation of the x-ray radiation by the constituents of rock sample 104. While FIG. 3a illustrates one 2D slice image 300, 3D digital image volume 128 of rock sample 104 is typically composed of multiple 2D slice images at locations stepped along one axis of rock sample 104 (e.g., a "stack" of multiple 2D slice images), together forming a 3D image of rock sample 104. The combining of the 2D slice images into 3D digital image volume 128 may be performed by computational resources within imaging device 122 itself, or by computing device 120 from the series of 2D slice images 128 produced by imaging device 122, depending on the particular architecture of testing system 102.

In block 206, the testing system 102 performs segmentation or other image enhancement techniques on digital image volume 128 of rock sample 104 to distinguish and label different components or phases of image volume 128 from the grayscale values of the image. More specifically, computing device 120 performs this segmentation in order to identify components, such as pore space and mineralogical components (e.g., clays and quartz). In some embodiments, testing tool 130 is configured to segment image volume 128 into more than two significant phases, representing such material constituents as pore space, clay fraction, quartz fraction, other various mineral types, organic matter, or composite materials.

Figure 3B:
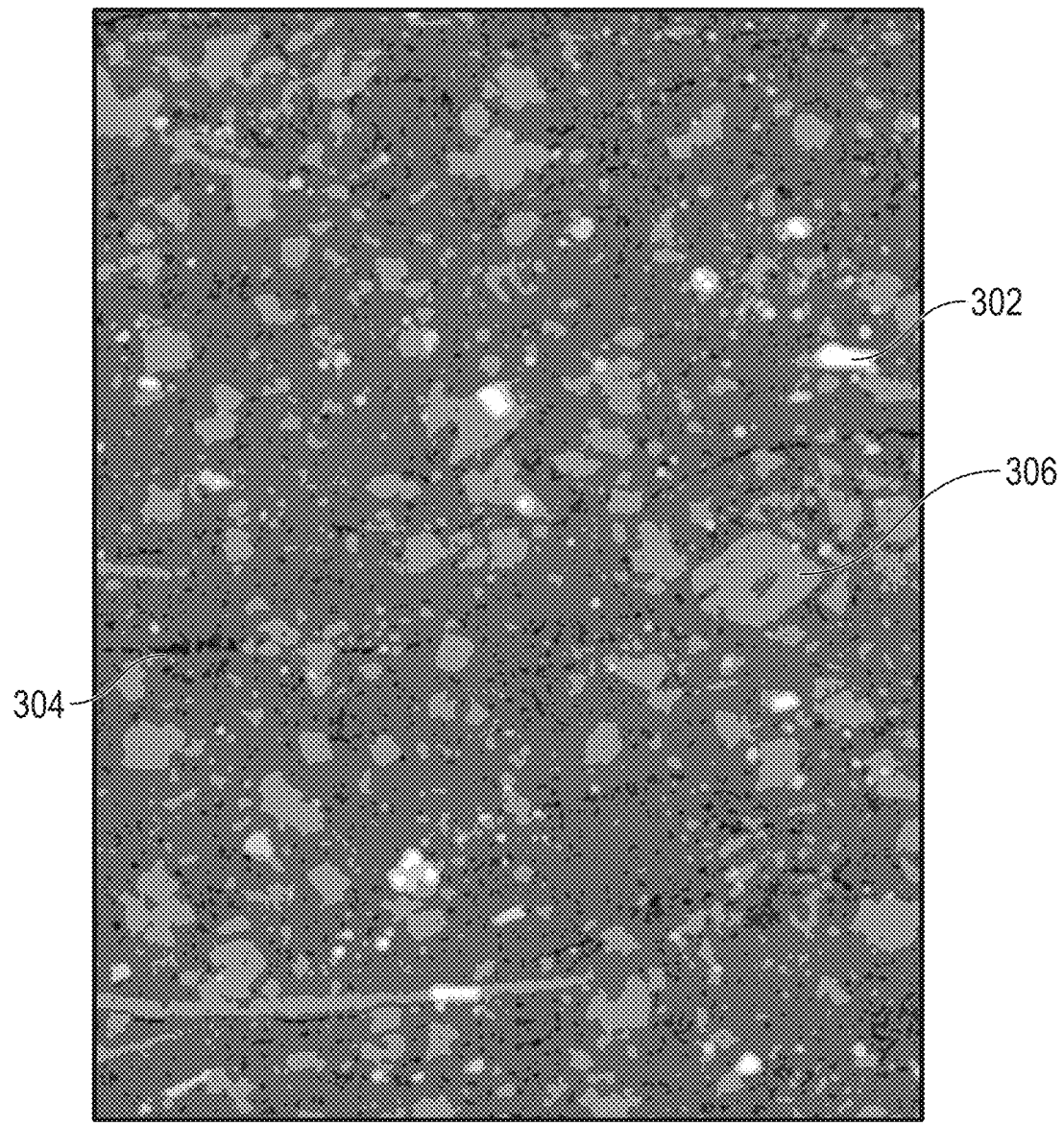

The computing device 120 can utilize any of a number of types of segmentation algorithms. One approach to segmentation is the application of a "thresholding" process to image volume 128, in which computing device 120 chooses a threshold value within the voxel amplitude range. Those voxels having an amplitude below the threshold value are assigned one specific numeric value that denotes pore space, while those voxels having an amplitude above the threshold are assigned another numeric value that denotes matrix space (i.e., solid material). In another example, there are multiple threshold values that define a number of different voxel amplitude ranges. In this approach, thresholding converts a grayscale image volume to a segmented volume of voxels having one of two (or more) possible numeric values, commonly selected to be 0 and 1. FIG. 3b illustrates an example of the segmentation performed on a 2D slice image 310 (e.g., part of 3D digital image volume 128) via thresholding with more than two possible numeric values. As illustrated, segmentation allows the structural details of a rock sample to be distinguished, in this example with the solid material 302 shown in white, and pores or void space 304 shown in black, and partial solid/pore space 306 shown in light and dark greys. Further segmentation can be applied one or more times to differentiate various features within a grayscale image. If simple thresholding is used, multiple threshold values can distinguish among different materials exhibiting different x-ray attenuation characteristics, such as clay, quartz, feldspar, etc.

Computing device 120 may alternatively utilize other segmentation algorithms. An example of such an alternative algorithm is known in the art as Otsu's Method, in which a histogram-based thresholding technique selects a threshold to minimize the combined variance of the lobes of a bimodal distribution of grayscale values (i.e., the "intra-class variance"). Otsu's method can be readily automated, and may also be extended to repeatedly threshold the image multiple times to distinguish additional material components such as quartz, clay, and feldspar. Other examples of automated segmentation algorithms of varying complexity may alternatively or additionally be used by computing device 120 to distinguish different features of an image volume, such algorithms including Indicator Kriging, Converging Active Contours, Watershedding, and the like.

The computing device 120 may also utilize other image enhancement techniques to enhance or improve the structure defined in image volume 128 to further differentiate among structure, to reduce noise effects, and the like. Likewise, while computing device 120 can perform the segmentation or other image enhancement techniques, it is contemplated that other components of testing system 102, for example imaging device 122 itself, may alternatively perform image enhancement in whole or in part.

Segmentation thus associates the voxels in the digital image volume 128 with the particular material (or pore space, as the case may be) at the corresponding physical location within rock sample 104. Each voxel is labeled with one unique material identification corresponding to the particular constituent assigned to a given x-ray attenuation amplitude. Such constituents including pore space, matrix material, mixed pore-clay fraction, individual grains, grain contacts, mineral types, and the like.

Figure 4:
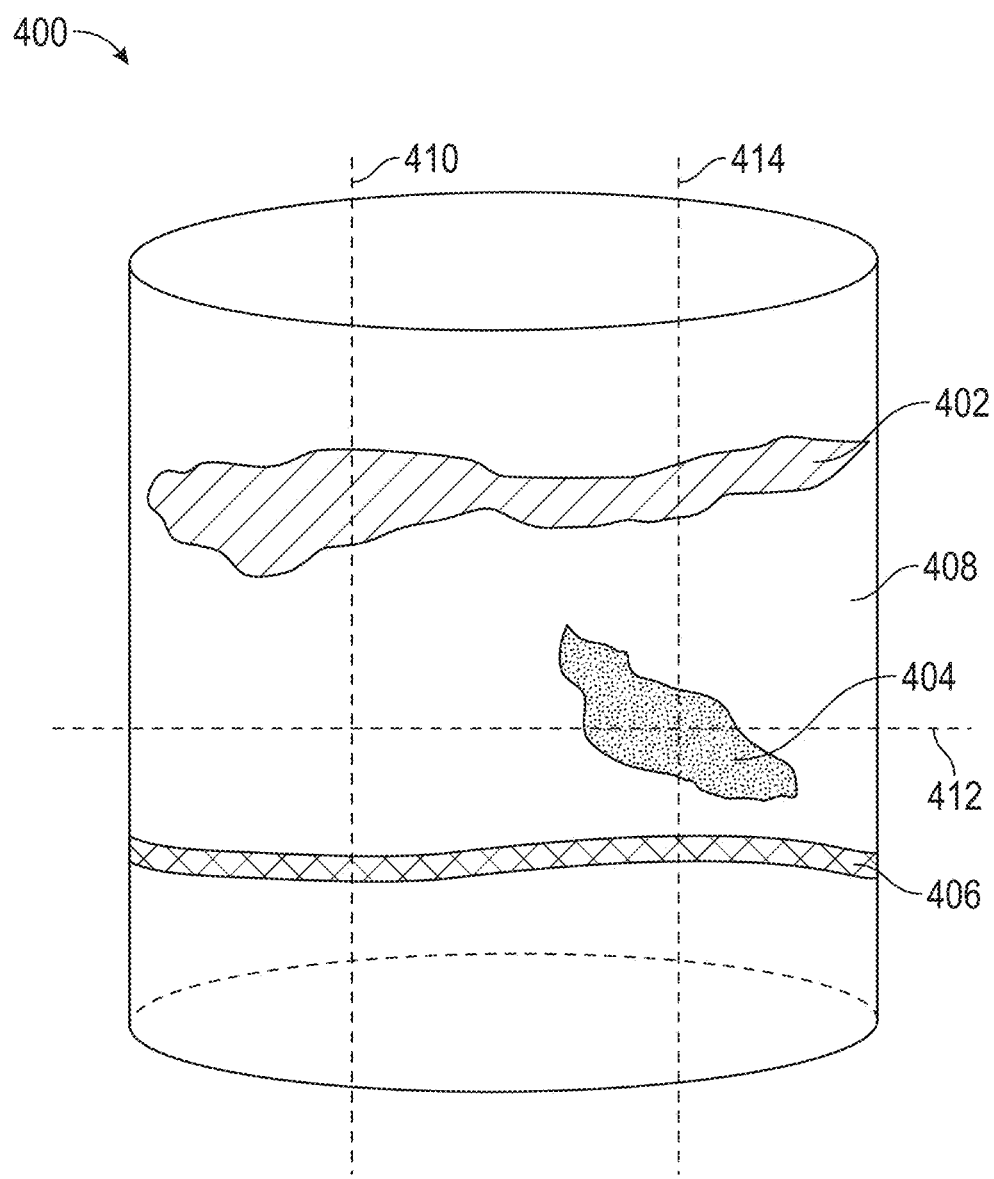
FIG. 4 shows the rock sample including a plurality of rock fabrics, in preparation for machining in accordance with various embodiments disclosed herein.

FIG. 4 shows a representation 400 of digital image volume 128 of the rock sample 104. As explained above, the digital image volume 128 may be constructed from a series of 2D slice images 300 (or segmented 2D slice images 310). The representation 400 includes different rock fabrics, for example that correspond to the identified rock fabrics from the 2D slice images 300. In some examples, a fabric refers to a pattern shared by a "region" or portion of an image. For example, a region may be grouped together as a fabric based on sharing underlying attributes such as porosity, compositional phases and their proportions, image entropy, and the like. Certain specific examples of rock fabrics include pore space and various types of solids. For example, different types of solid material may correspond to different rock fabrics. Thus, a fabric may be considered as a quantification of spatial patterns of pixel values (e.g., pixel intensity) within a particular domain or image.

In the example of FIG. 4, the representation 400 includes a first rock fabric 402, a second rock fabric 404, and a third rock fabric 406, as well as a host or depositionally-dominant sedimentary rock fabric 408, which makes up the bulk of the rock sample between the rock fabrics 402, 404, 406. At least some of the voxels that comprise the representation 400 are associated with or mapped to a physical coordinate space associated with the rock sample 104. This allows for a mapping of the imaged rock fabrics 402, 404, 406 to specific physical locations within the rock sample 104.

Embodiments of the present disclosure leverage the location of imaged rock fabrics 402, 404, 406 in the representation 400 of the digital image volume 128 to identify one or more digital planes through the digital image volume 128 that intersect with the rock fabrics 402, 404, 406, as shown in block 208 of FIG. 2A. In some examples, the segmentation described above, performed in block 206 of FIG. 2A, provides the spatial identification of these fabrics 402, 404, 406. Following segmentation, and depending on the complexity and arrangement of rock fabrics 402, 404, 406 within the digital image volume 128, multiple digital planes may be required to adequately intersect all of the different rock fabrics 402, 404, 406. Further, in some examples, digital plane(s) are identified that reduce or minimize the number of plane(s) needed to adequately intersect all of the different rock fabrics 402, 404, 406.

For example, to intersect the rock fabrics 402, 404, 406, a first set of digital planes includes digital plane 410, which intersects the rock fabrics 402, 406, and digital plane 412, which intersects the rock fabric 404. However, it may be advantageous to reduce the number of digital planes if possible, to reduce subsequent machining and SEM imaging requirements. Thus, in at least one embodiment, a digital plane 414 is selected that intersects the rock fabrics 402, 404, 406, reducing the required machining and imaging to adequately image all the rock fabrics 402, 404, 406.

After the digital plane 414 is identified (e.g., according to block 208 of FIG. 2A), the method 200 continues in block 210 in which the physical rock sample 104 is machined (or otherwise mechanically prepared) to expose a physical face that corresponds to the identified set of digital planes (e.g., digital plane 414). As noted above, since the digital image volume 128 (e.g., its composite voxels) is mapped to the physical coordinate space associated with the rock sample 104, the identified digital plane 414 corresponds to a plane in that physical coordinate space, making it relatively straightforward to machine the corresponding physical face.

Figure 5A:
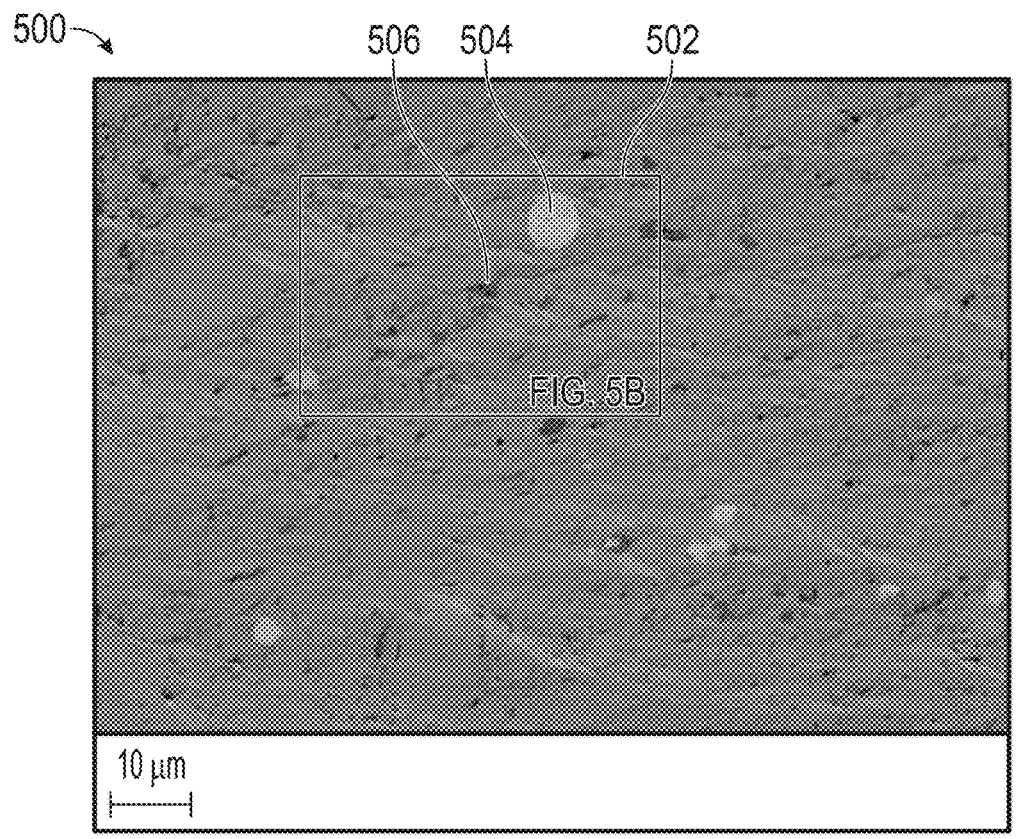
FIGS. 5a-5c show scanning electron microscope (SEM) images of a machined rock surface at different scales in accordance with various embodiments disclosed herein.
Figure 5B:
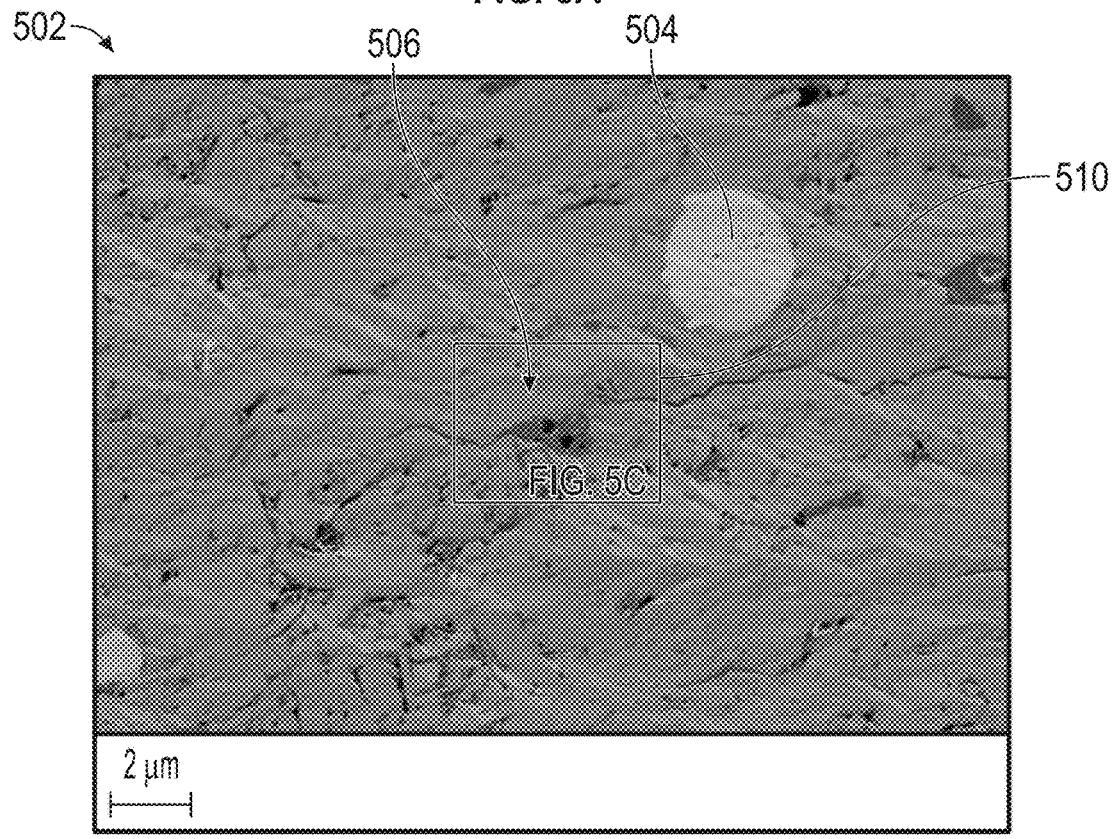
Figure 5C:
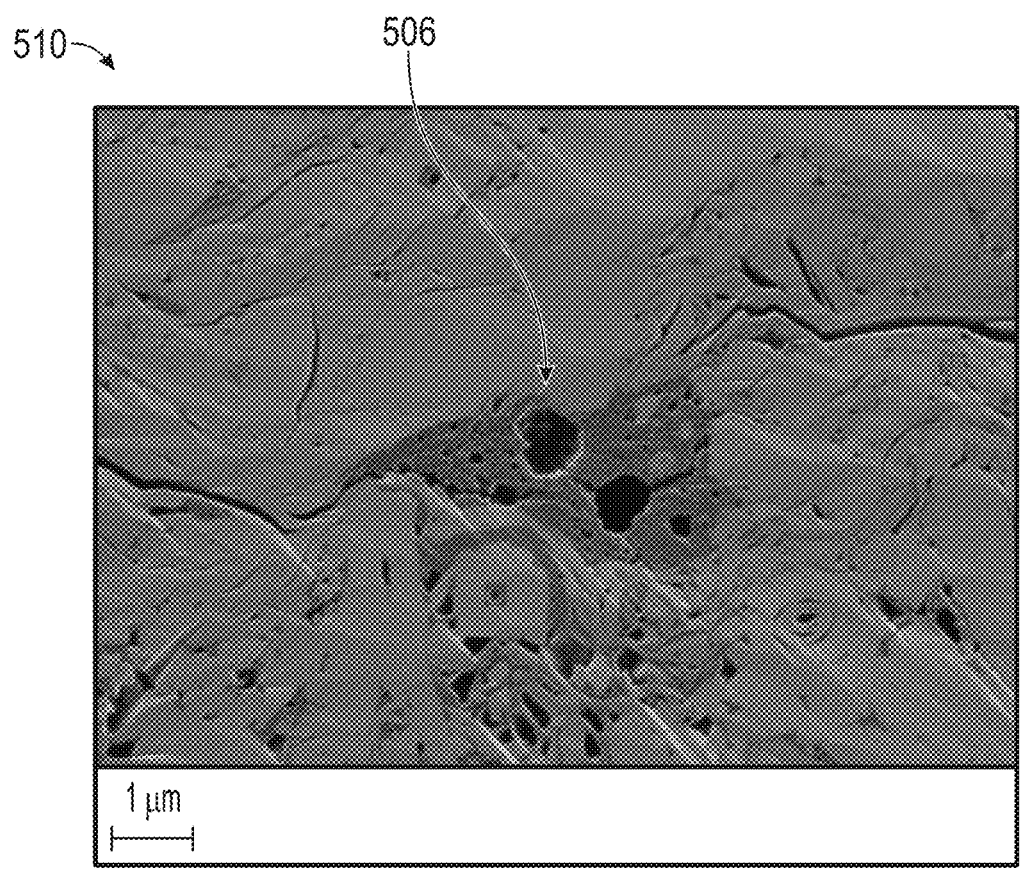

Once the physical rock sample 104 has been machined or otherwise mechanically prepared to expose one or more physical faces that correspond to the identified set of digital planes, the method 200 continues in block 212 with obtaining a series of SEM images of the physical face(s). In various embodiments, the SEM imaging of the physical face(s) of the rock sample 104 is performed at a variety of scales (e.g., sequential SEM imaging with increasing amounts of zoom into the physical face(s) of the rock sample 104). FIGS. 5a-5c demonstrate example SEM images captured at different (e.g., sequentially zoomed in) scales, which assist in defining the spatial characterization of one or more rock fabrics (e.g., fabrics 402, 404, 406 in FIG. 4) in the digital plane 414.

In one example, the regions that are zoomed into may vary depending on the circumstances of the imaging being performed. In one example in which organic porosity is of particular interest for a given project, an emphasis is placed on acquiring zoomed-in images of regions that appear to include fabric(s) of that type. Continuing this example, regions that do not appear to include fabric(s) demonstrating organic porosity are less frequently sampled (i.e., fewer zoomed-in images are acquired of regions that do not appear to include volumes of fabric(s) including organic porosity of at least a threshold amount, and a level of zoom for those regions not including at least a threshold amount of fabric(s) demonstrating organic porosity may also be lower). In another example, overall pore connectivity is of particular interest for the given project. In this example, all regions may be equally sampled to avoid overlooking image data that is relevant to a determination of pore connectivity. One example of equal sampling includes acquiring zoomed in images along a rectangular grid path with regular spacing across the dimensions of an image.

FIG. 5a shows a SEM image 500, which is approximately 100 microns wide. A first zoom portion 502 of the SEM image 500 contains multiple rock fabrics, including a first fabric 504 and a second fabric 506. For example, the first fabric 504 corresponds to an inorganic, porosity-rich fabric while the second fabric 506 corresponds to an organic, porosity-rich fabric. The zoom portion 502 may be identified as a result of containing a particular fabric of interest having finer details not easily discernable at lower resolutions. For example, the zoom portion 502 may be selected from the SEM image 500 because it indicates the presence of organic rich porosity. The zoom portion 502 provides greater visual clarity on the structure of the organic pores compared to what can be discerned from the SEM image 500. Further zooming-in may sometimes be useful to discern sufficient structural detail for various regions of interest.

FIG. 5b shows the first zoom portion 502 in greater detail. For example, the greater detail in FIG. 5b is obtained by subjecting the first zoom portion 502 to SEM imaging at a higher zoom level, and thus the first zoom portion 502 is equivalently a zoomed SEM image 502. In particular, as shown in FIG. 5b, the zoomed SEM image 502 is approximately 50 microns wide. In FIG. 5b, the first and second fabrics 504, 506 are seen as larger, and in greater detail. Further, a second zoom portion 510 is identified in a manner similar to that in which the first zoom portion 502 was identified in FIG. 5a. For example, the second zoom portion 510 may be selected from the zoomed SEM image 502 as a result of the second zoom portion 510 having a higher diversity of represented rock fabrics than other portions of the zoomed SEM image 502.

FIG. 5c shows the second zoom portion 510 in greater detail. For example, the greater detail in FIG. 5c is obtained by subjecting the second zoom portion 510 to SEM imaging at a higher zoom level, and thus the second zoom portion 510 is equivalently a second zoomed SEM image 510. In particular, as shown in FIG. 5c, the second zoomed SEM image 510 is approximately 10 microns wide. The first fabric 504 is not present in the second zoomed SEM image 510 because it was not included in the second zoomed portion 510 in FIG. 5b. However, the second fabric 506 is seen as larger and in greater detail. In the example of FIG. 5c, the identified second fabric 506 in the central area of the second zoomed SEM image 510 is illustrative of an organic-rich pore fabric, which may impact or contribute to the flow, transport, and storage descriptions of the larger rock sample 104.

Although the example of FIGS. 5a-5c includes a first and second zoomed image 502, 510, other examples of this disclosure may extend to additional or fewer iterations of zooming as required to capture a sufficient level of diversity of represented rock fabrics. Further, the process or capturing multiple zoomed SEM images may be repeated across the physical face(s) of the larger rock sample 104. For example, a set of SEM images zoomed to the level of that shown in FIG. 5c may be obtained over the area represented by the SEM image 500 of FIG. 5a. Thus, a set of zoomed SEM images, across multiple scales (e.g., "multi-scale") is produced, which captures the finer detail of the physical face(s) of the larger rock sample 104. This set of multi-scale SEM images may include at least a threshold number of rock fabrics of the plurality of rock fabrics contained in the digital image volume 128, described above. A higher threshold in this context results in a set of multi-scale SEM images that captures or represents a larger percentage (e.g., about 70%, 80%, 90%, or 100% in some cases) of the fabrics in the digital image volume 128. A lower threshold in this context results in a set of multi-scale SEM images that captures or represents a relatively lower percentage (e.g., less than about 70%) of the fabrics in the digital image volume 128, for example to reduce computational or processing resources required for subsequent steps of the method. Additionally, as will be explained further below, segmentation may be performed on the second zoomed SEM image 510 to extract characteristic quantities (e.g., pore space, organic solid material, and solid inorganic material), which may be leveraged for further numerical predictions or determinations related to the larger rock sample 104.

Figure 5D:
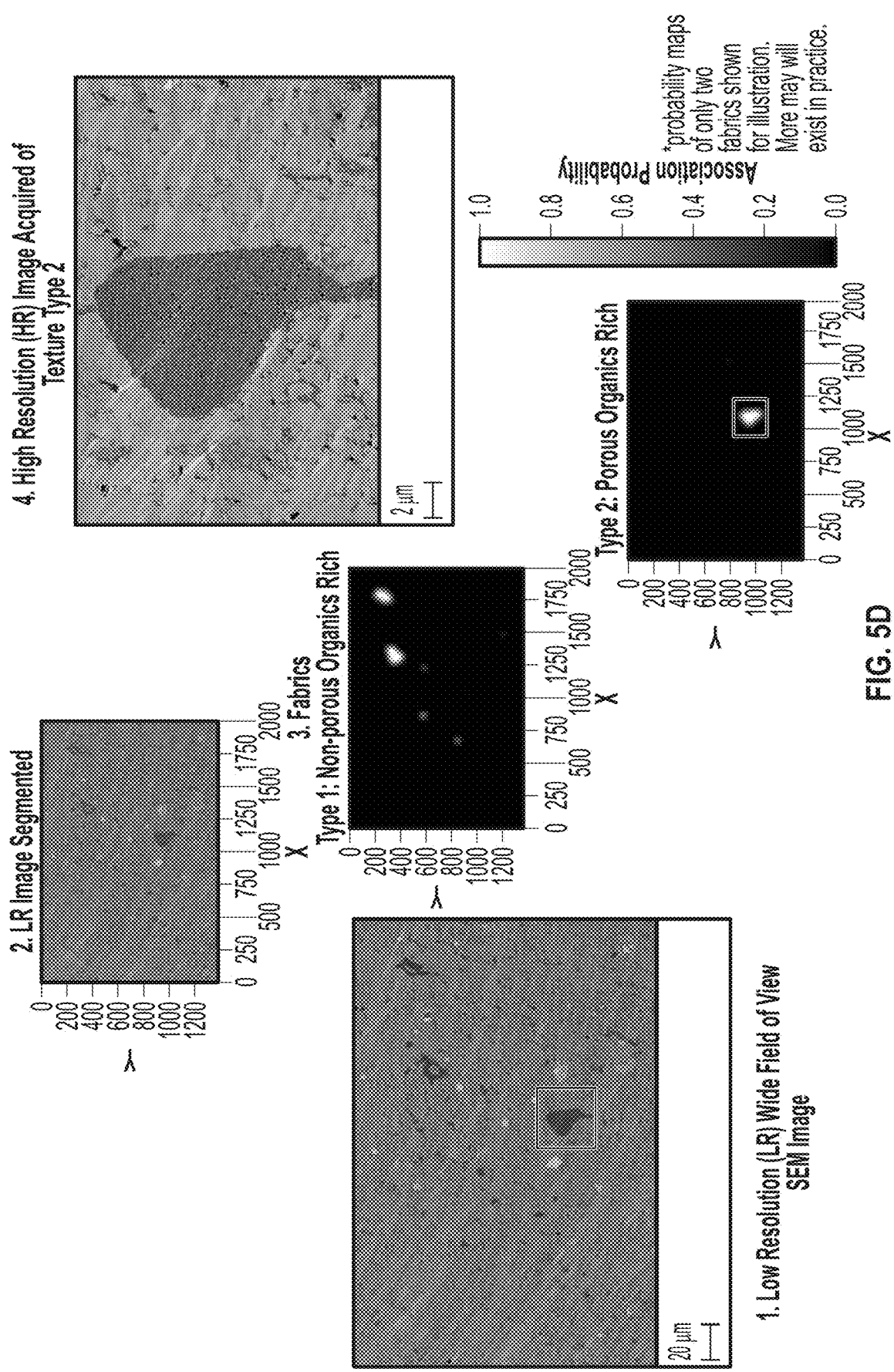
FIG. 5d shows an alternate example of the process of FIGS. 5a-5c in accordance with various embodiments disclosed herein.

FIG. 5d provides an alternate example of the process shown in FIGS. 5a-5c and described above. In particular, in step 3 of FIG. 5d, a probability map is generated (e.g., using an unsupervised learning algorithm) based on a segmented, lower-resolution image obtained in step 2 of FIG. 5d. The probability map of step 3 probabilistically groups similar fabrics. For example, the type 1 probability map illustrates the probability of whether a region is a non-porous organic-rich fabric, while the type 2 probability map illustrates the probability of whether a region is a porous, organic-rich fabric. In some cases, a grouping of similar fabrics indicates or identifies a region of interest of the rock sample 104 for higher-resolution imaging. In the example of FIG. 5d, this identified region of interest corresponds to the boxed region in the lower portion of the type 2 material, which is shown to have a high probability of being a similar rock fabric. In one example, the identified region of interest, or first area within the SEM image, contains a first number of pixels that are associated with a primary fabric type (e.g., porous, organic-rich fabric in the case of the type 2 probability map) and a second number of pixels associated with fabrics other than the primary fabric type. Thus, the region of interest may be identified based on the ratio of the first number to the second number being above a threshold, which indicates a certain percentage (or more) of the primary fabric type in that region. Once the regions of interest is identified, additional SEM imaging may be performed at higher (e.g., finer) resolutions, as shown in step 4 of FIG. 5d.

Referring generally to FIGS. 5a-5d, some examples of this description leverage one or more machine learning algorithms to determine various aspects of the zoom-and-capture processes described above. For example, the number of rock fabrics to be sampled (e.g., of a total number of identified fabrics in the digital image volume 128) may be determined responsive to application of a machine learning algorithm. Similarly, the resolution at which to capture certain rock fabrics (e.g., how much zooming in is appropriate for a given rock fabric) may be determined responsive to application of a machine learning algorithm. In one example, these values or levels are determined in an iterative fashion, to produce a data set that is able to be processed in a reasonable amount of time (e.g., avoiding a brute force-sampling of all possible combinations of numbers of fabrics to capture, and resolutions at which to capture those fabrics), while still providing useful data of each of a certain number of fabrics. For example, this avoids conditions such as under-zooming a first fabric, thus missing out on important detail of that fabric; or over-zooming a second fabric and thus wasting valuable time and processing resources (either during capture and/or subsequent processing of a too-detailed image).

Figure 6A:
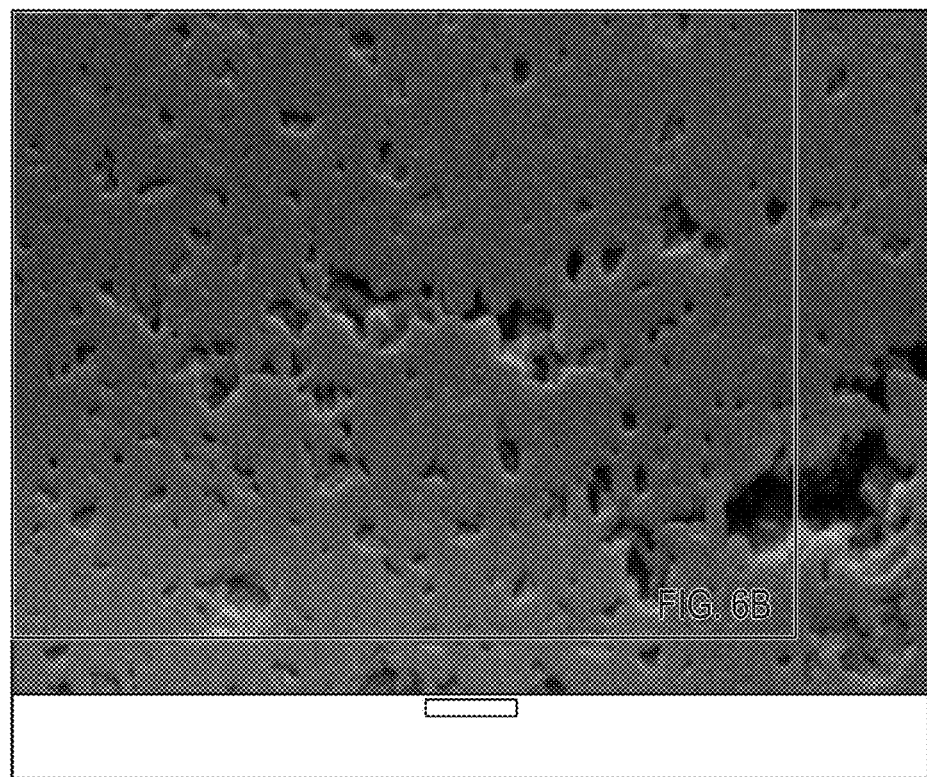
FIGS. 6a and 6b demonstrate performing a segmenting operation on a SEM image in accordance with various embodiments disclosed herein.
Figure 6B:
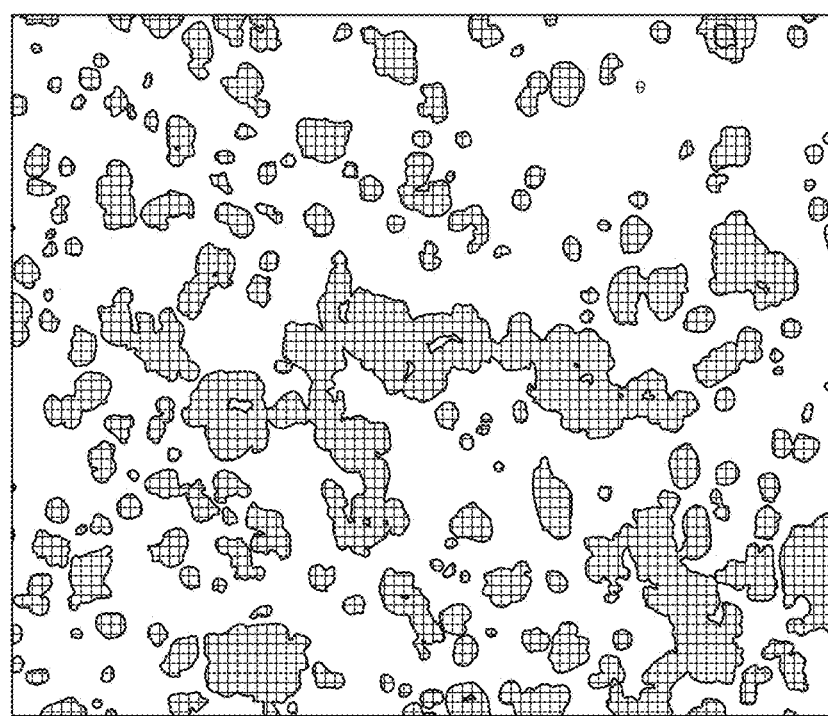

Referring back to the method 200 of FIGS. 2A and 2B, once a set of SEM images is obtained at a resolution of approximately 2-4 times the smallest pore or other material feature of interest to be analyzed for a given application, the method 200 continues in block 214 with optionally applying segmentation to the 2D SEM images. For example, if characterizing microporosity of a sample (e.g., pore sizes of less than 5 nm), the required resolution may be approximately 2 nm. As another example, if characterizing pyritic pores of larger than 15 nm, the required resolution may be approximately 5 nm, and thus the level of required zoom may be relatively more relaxed. Segmenting the 2D SEM images is similar to the segmentation described above with respect to block 206 and FIGS. 3a and 3b, regarding segmenting the 2D slice image 300. FIG. 6a shows an exemplary simple, two-constituent (e.g., pore space and organic matter) SEM image 600, which may be at a scale similar to the second zoomed SEM image 510 described above with respect to FIG. 5c. In this example, where the SEM image 600 is relatively simple, segmentation may be performed with a single threshold to distinguish between pore space and organic matter. FIG. 6b shows a resulting segmented SEM image 610 in which pore space is shown as black and organic matrix material is shown as white. By segmenting the SEM images obtained in block 212 into two phases (e.g., pore space and organic matter), the pore space of the larger rock sample 104 is captured at a fine level of granularity in two dimensions, which may then be leveraged to create a 3D digital model volume that represents the rock sample 104, but at a finer resolution (e.g., greater level of detail) that that of the initially captured digital image volume. In particular, the segmented 2D SEM image 610 in FIG. 6b may be used as a training image for a 2D-to-3D volume transformation, which is explained in further detail below. In other examples, the SEM images obtained in block 212 may be segmented into an arbitrary number of phases, representing various rock fabrics.

Figure 7A:
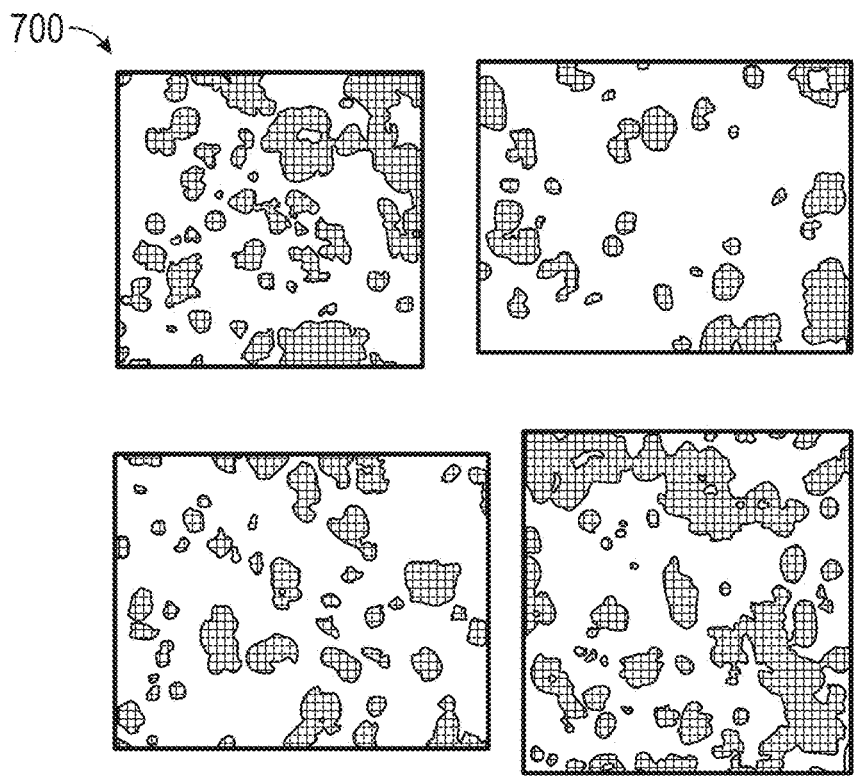
FIGS. 7a and 7b demonstrate generating a set of statistically similar 3D models from a set of segmented SEM images in accordance with various embodiments disclosed herein.

FIG. 7a shows a set 700 of segmented 2D SEM images, similar to the segmented SEM image 610 explained above. The set of 2D SEM images 700 are extracted from multiple SEM images that contain differing representations of a particular fabric (e.g., 402, 404, 406). Referring back to the method 200, in block 216 the set of segmented 2D SEM images 700 is used to generate a set of statistically-similar 3D digital model volumes for a particular rock fabric. In certain examples, one or more stochastic algorithms (e.g., a cross-correlation function) are applied to the set of 2D SEM images 700 to generate realizations of statistically-similar or statistically-equivalent 3D pore-organic matrix volumes. In the example of the cross-correlation function, this process uses structural information (e.g., data indicative of correlation between different parts of the image) in the 2D training images (e.g., the 2D SEM image 610 described above) to first break up the images into smaller constituent areas and then recombine those areas in a stochastic manner to synthetically generate statistically similar, but non-identical, versions of the original 2D training image. Subsequently, the original 2D training image, as well as its statistically similar versions, are projected into one or more imaginary planes (e.g., in 3D). These 3D projections, or "digital model volumes," may be used to statistically condition a subsequent iteration of generating synthetic, statistically similar images. In one example, such a conditioning process is useful to iteratively generate synthetic images that may be overlain or underlain with previously generated synthetic images in a manner that appears to more accurately reflect a natural look and/or structural continuity of a real-world rock sample.

Figure 7B:
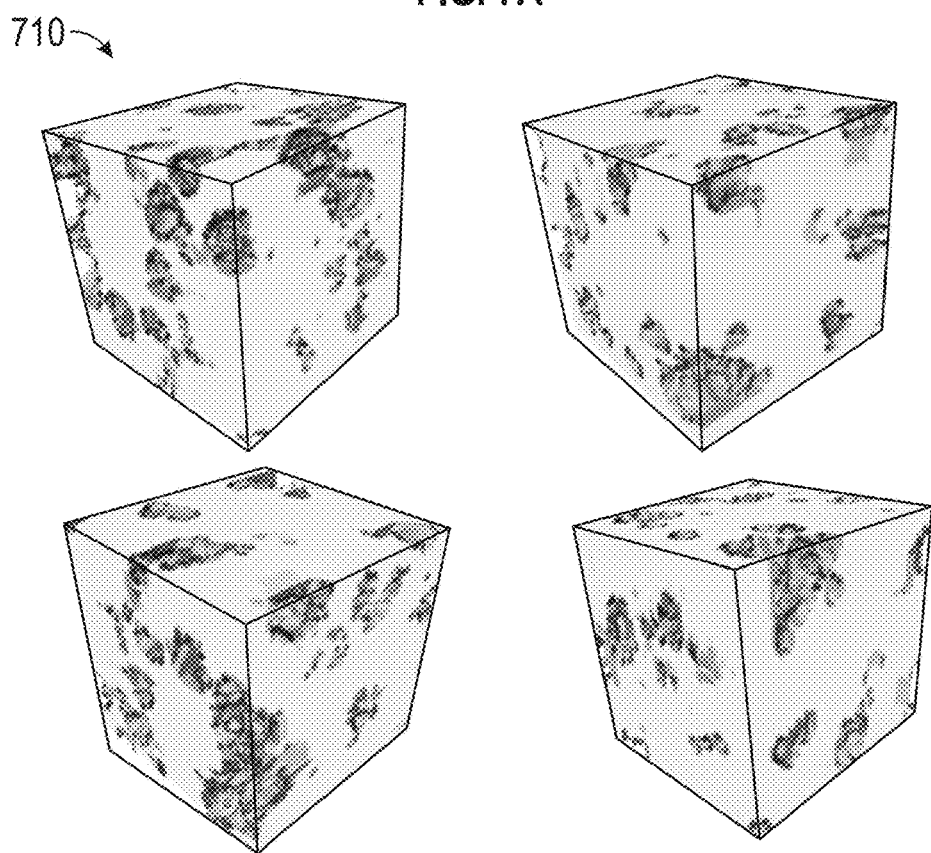

FIG. 7b shows an exemplary set 710 of 3D pore-organic matrix model volumes, which are statistically-similar to each other. For example, a first digital model volume is statistically similar to a second digital model volume when attributes such as the variogram of the pore phase of the first model volume and that of the second model volume are identical, or within a threshold amount (e.g., based on an engineering tolerance). In some cases, statistical equivalence is controlled by an assumption regarding ergodicity in the stochastic algorithm. Because the set 710 of 3D digital model volumes for a given fabric type is generated computationally from 2D images taken from a single physical face or a small number of physical faces of the rock sample 104, the set 710 may be generated much more easily and with relatively less expense than, for example, FIB-SEM in which a portion of rock material is continually machined and imaged layer-by-layer. In some examples, a numeric value of a voxel in the 3D digital model volume(s) of the set 710 is determined based on a spatial distribution of pixel values in each of the 2D SEM images used to generate the 3D digital model volume(s). In one specific, but non-limiting example, a circular grain in the 2D SEM images (e.g., 100 white pixels in an approximate circle surrounded by black pixels) leads to the generation of a spherical grain in the 3D digital model volume (e.g., 1000 white voxels in an approximate sphere surrounded by black voxels).

Additionally, because the set 710 of 3D digital model volumes for a given fabric type may be generated computationally from 2D images taken from multiple physical faces of the rock sample 104, such 2D images may be of different axial orientations of the rock sample 104. In one specific, but non-limiting example, a first 2D SEM image is taken of a physical face of the rock sample 104 along a first axis with respect to a position of the rock sample 104, while a second 2D SEM image is taken of a physical face of the rock sample 104 along a second axis with respect to the position of the rock sample 104. This enables the generated 3D digital model volume(s) to consider features that may differ in their axial symmetry. For example, a feature that appears circular along one axis might typically be represented as spherical in the resultant 3D digital model volume. However, if that same feature appears oblong along another axis, that feature may instead be represented as ovoid in the resultant 3D digital model volume.

Additionally, the process to generate the set 710 of 3D digital model volumes for a given fabric type may be repeated for multiple fabric types, which results in a plurality of (e.g., N) realizations of each of a plurality of (e.g., M) fabric types. The N realizations of 3D digital model volumes for a given fabric type represent a number of possibilities of what a 3D version of that fabric type may look like in nature, which provides a way to calculate or determine petrophysical properties at a fabric level and thus generate a probability distribution of various petrophysical properties for that particular fabric type. In some cases, estimates of petrophysical properties determined from the 3D digital model volumes are more accurate than estimates of those same properties derived from 2D models. As a result, the generation of the 3D digital model volumes described herein improves accuracy relative to, for example, estimating petrophysical properties based on 2D SEM images.

Relative to the original digital image volume 128, the 3D digital model volumes in the set 710 have a higher (e.g., finer) resolution due to being generated based on 2D SEM images. Additionally, each 3D digital model volume is specific to one fabric type of the often-multiple fabric types present in the digital image volume 128.

Once a set of statistically-similar 3D models 710 are generated, the method 200 continues in block 218 with performing numerical simulation on the 3D digital model volumes 710 to determine one or more material or petrophysical properties associated with each of the 3D digital model volumes 710. In one example, the 3D digital model volumes 710 are used as a modeling grid for one type of rock fabric (e.g., N realizations of one fabric type) to determine the desired material property or properties for that fabric type. In various examples, the material property may include porosity, pore size distributions, permeability, capillary pressure, electric resistivity, and elastic moduli.

The following exemplary Table 1 demonstrates representative porosity and permeability values as material properties derived from a set of 3D pore-organic matrix volumes 710 shown in FIG. 7b. In this example, the 3D pore-organic matrix volumes 710 are used to calculate porosity and/or permeability using one or more image analysis algorithms such as, for example, segmentation (e.g., for porosity) and Lattice-Boltzmann simulation (e.g., for permeability). In an example, the set of computed values that result from the application of these algorithms represents a full range of possible porosities and permeabilities that may be encountered in real-world rock samples that include that fabric. Thus, the algorithms produce or provide a probability distribution for each of porosity and permeability for a particular fabric type (e.g., porous organic-matter in this example). Generating additional realizations, or digital model volumes, results in the ability to determine petrophysical properties based on a larger number of models, and to thus produce a correspondingly larger dataset of probability distributions. This results in a more accurate and/or precise determination of probability distributions for those petrophysical properties.

TABLE 1

| Realization | Permeability (m$^2$) | Porosity (% volume) |
|---|---|---|
| 1 | 3.29E−19 | 22.24 |
| 2 | 3.78E−19 | 23.38 |
| 3 | 3.37E−19 | 21.28 |
| 4 | 5.08E−19 | 25.64 |
| 5 | 4.93E−19 | 25.84 |
| 6 | 3.91E−19 | 23.39 |
| mean | 4.1E−19 | 23.63 |

Each realization in Table 1 corresponds to one of the 3D models of the example set 710 of 3D models. The statistical similarity of the various models is reflected by the relatively close grouping of permeability and porosity values for each of the realizations in Table 1. In some examples, the numerical simulation utilizes proprietary algorithms from exemplary direct numerical simulation techniques. For example, a two-phase lattice Boltzmann simulation may be utilized to estimate a numeric permeability based on the 3D digital model volume(s) for a given fabric type, while an object partitioning and point counting algorithm may be utilized to estimate a numeric pore size distribution based on the 3D digital model volume(s) for a given fabric type.

In some examples, the determined material property or properties for a given rock fabric is associated with voxels in a 3D digital model volume that correspond to that given rock fabric. Additionally, locations within the digital model volume(s) may also be mapped to the physical coordinate space associated with the rock sample 104. Thus, the determined material property or properties can be associated with the physical coordinate space associated with the rock sample 104. As described above, the material property mapped to a particular voxel in the digital model volume(s) may be sampled from a distribution of properties measured for the given rock fabric, which results in the digital model volume(s) being a composite volumetric grid of such material properties.

Figure 8:
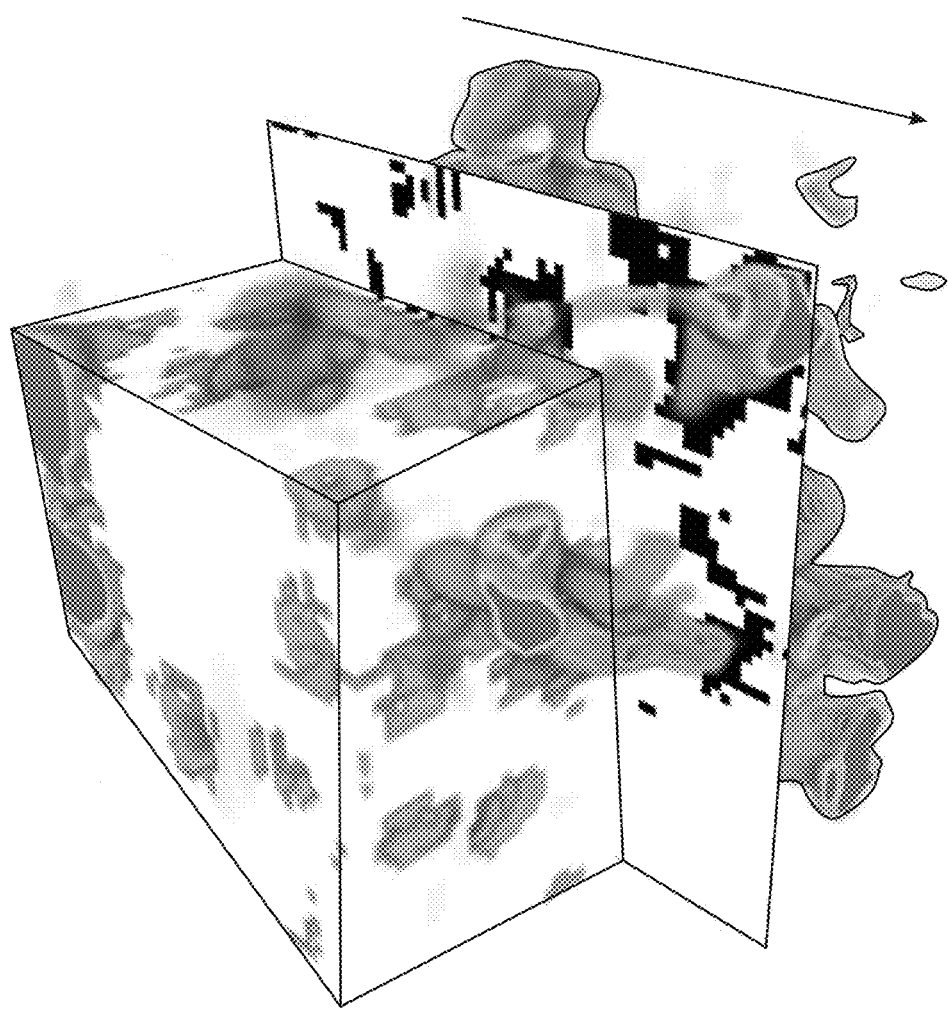
FIG. 8 shows a visual representation of a digital numerical simulation performed on one of the 3D models from FIG. 7b in accordance with various embodiments disclosed herein.

FIG. 8 shows an exemplary 3D model (e.g., one of the example sets 710 of 3D models), in which a flow field (e.g., the determined material property) as a greyscale heat map is superimposed on the 3D model. In general, a flow field comprises a flow velocity value for multiple voxels (e.g., each voxel) in a 3D digital model volume. A permeability tensor is a simplification of a 3D flow field to a representative value (e.g., a single value in some cases), and thus may be calculated responsive to a determined flow field for a given 3D digital model volume. Although the porosity of the 3D model in FIG. 8 appears disconnected, the flow field demonstrates that there are flow pathways through the 3D volume. The greyscale heat map represents the flow velocity, with darker tones representing a higher velocity and lighter tones representing a lower velocity. The arrow in FIG. 8 represents the overall direction of the flow being modeled through the 3D volume.

Figure 9:
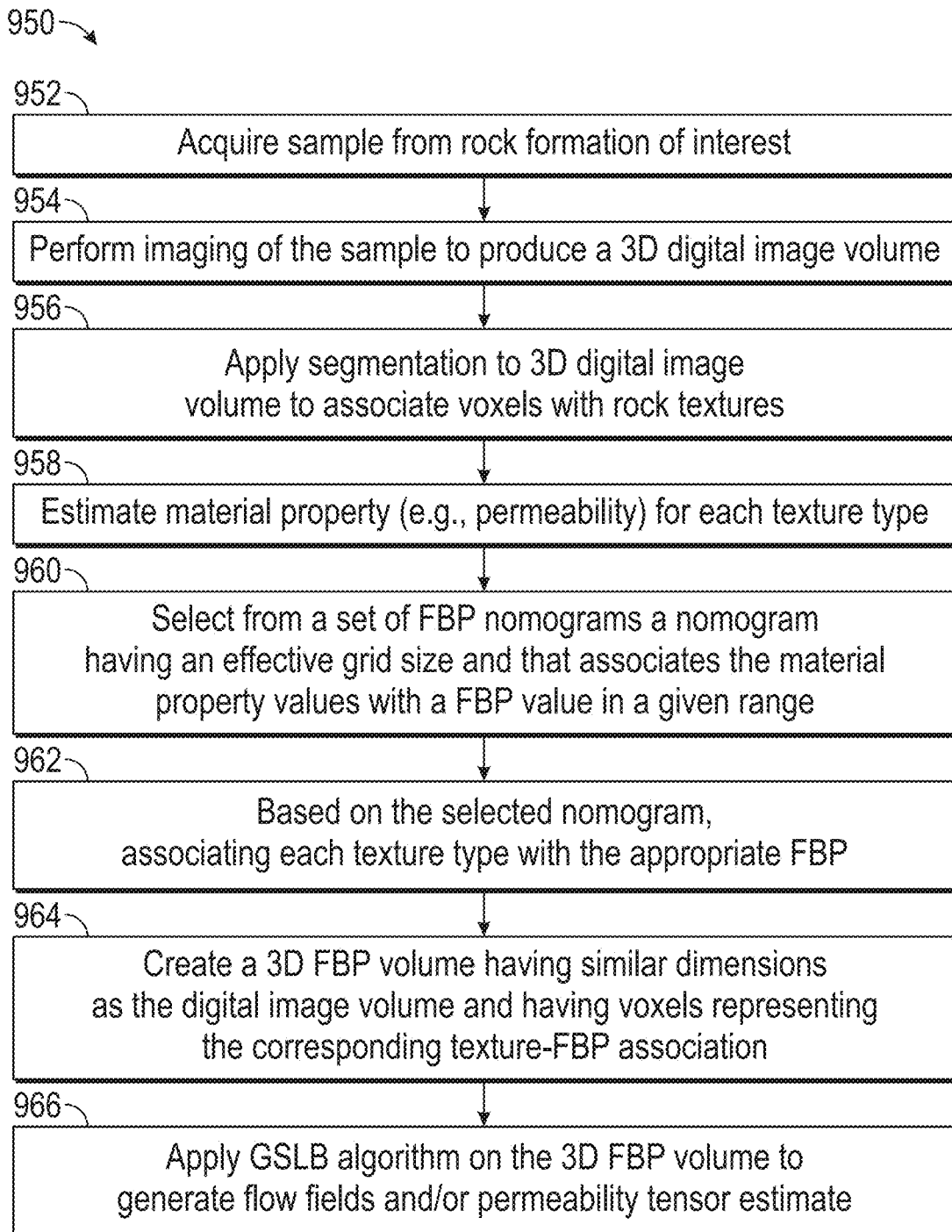
FIG. 9 shows a flow diagram for another method for analyzing rock samples in accordance with principles disclosed herein.

FIG. 9 shows a flow diagram of a method 950 for analyzing rock samples in accordance with principles disclosed herein. FIG. 9 contains certain steps that are similar to those described above with respect to FIGS. 2A and 2B. Though depicted sequentially as a matter of convenience, at least some of the actions shown can be performed in a different order and/or performed in parallel. Additionally, some embodiments may perform only some of the actions shown. In some embodiments, at least some of the operations of the method 950, as well as other operations described herein, can be implemented as instructions stored in a computer readable medium and executed by one or more processors 152.

Blocks 952, 954, and 956 are similar to blocks 202, 204, and 206, respectively, and description of those blocks is not repeated here for purposes of brevity.

In block 958, a material property is estimated for each of the rock fabrics associated in block 956 (and block 206). In the following examples, the material property is permeability; however, in other examples, different material properties for the rock fabrics may be estimated as described above. As described above with respect to block 218, numerical simulation may be performed on the 3D models 710 to determine such material properties (e.g., permeability), which are then associated with the various rock fabrics (or voxels representing those fabrics) of the digital image volume. In various examples, the material property may also include porosity, pore size distributions, permeability, capillary pressure, electric resistivity, and elastic moduli. As described above, the voxels of the digital image volume (and thus the associated, determined material property or properties) may be mapped to a physical coordinate space associated with the rock sample 104, improving understanding of the physical rock sample 104 and the formation from which it was sampled.

The method 950 continues in block 960 with selecting from a set of fractional bounceback parameter (FBP) nomograms a nomogram having an associated or effective grid size that associates the material property values determined in block 956 with an FBP value in a given range. For example, permeability values determined in block 956 span a permeability range. Each nomogram of the set of nomograms associates permeability values with FBP values for a given grid size. In some examples, the selected nomogram is the nomogram for which the permeability range is associated with FBP values between a lower FBP threshold and an upper FBP threshold.

Figure 10:
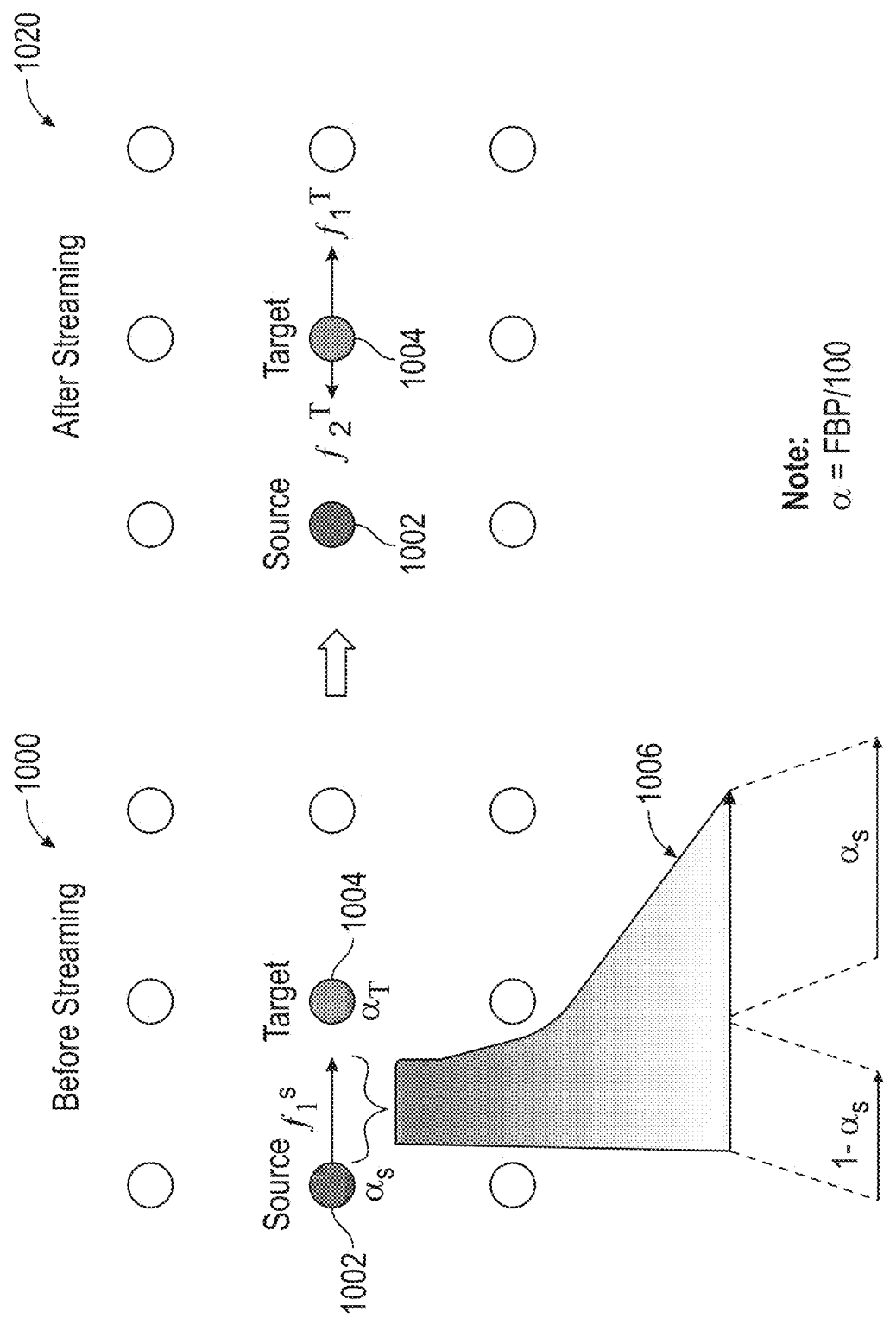
FIG. 10 shows an example of a fractional bounceback parameter (FBP) determination for use in a grayscale lattice Boltzmann (GSLB) model in accordance with principles disclosed herein.

FIG. 10 shows an example of an FBP determination for use in a grayscale lattice Boltzmann (GSLB) model or algorithm in accordance with principles disclosed herein. In FIG. 10, a grid of voxels is shown both before streaming (e.g., grid 1000) and after streaming (e.g., grid 1020). The streaming step is one step (e.g., an intermediate step) of the GSLB algorithm. "Before streaming" refers to the state of the GSLB output prior to mathematical application of the streaming function/operation. "After streaming" refers to the state of the GSLB output after application of the streaming function/operation. The streaming function/operation is a step at which the GSLB algorithm utilizes the FBP information provided in the primary input (e.g., from the original digital image/3D digital volume input). These primary inputs are represented by gridpoints (e.g., illustrated by circles in FIG. 10), as well as the specific FBP values associated with each of the gridpoints. In FIG. 10, the FBP values are illustrated by the shade of gray color at the gridpoints 1002 and 1004. In some examples, each gridpoint has an associated FBP value. In the example of FIG. 10, colorization of gridpoints is restricted to 1002 and 1004 is for purposes of simplification.

The GSLB algorithm is an iterative algorithm, and its output described above may be iteratively modified multiple times by multiple functions/operations. Streaming is one of the types of intermediate operations of the GSLB algorithm that performs such iterative modification. These iterative operations may be performed until required criteria are met, at which point the iteration stops (e.g., there are no additional iterations of the algorithm). During the iteration of the GSLB algorithm, the output at each step is also an input for a subsequent round of iteration. One component of this output is a set of fractional streaming values in different directions. For simplicity, only two directions: $f_1$ and $f_2$, have been illustrated in FIG. 10. $f_1^S$ is the fraction streaming from the source gridpoint 1002 towards the target 1004 gridpoint before the streaming function/operation is applied. $f_1^T$ is the fraction streaming from the target gridpoint 1004 towards a next gridpoint (e.g., to the right of the target gridpoint 1004) for the next round of iteration (e.g., after streaming is applied), while $f_2^T$ is the fraction streaming from the target gridpoint 1004 back towards the source gridpoint 1002 after streaming is applied. $f_1^T$ and $f_2^T$ are calculated by the streaming function/operation and are part of the inputs for a subsequent round of iteration. $\alpha_S$ and $\alpha_T$ are the decimal forms of the FBP at the source 1002 and target 1004 gridpoints, respectively.

The grid of voxels 1000, 1020 includes a source voxel 1002 and a target voxel 1004. In this example, a behavior of fluid flow is determined from the source voxel 1002 to the target voxel 1004. For example, it is previously determined (e.g., during a previous iteration of calculation) that the source voxel 1002 provides a flow in the direction of the target voxel 1004 of $f_1^S$, which may be rewritten as the sum of components $(1-\alpha_S)$ and $\alpha_S$, where $\alpha_S$ is equal to the FBP divided by 100.

As shown in the grid of voxels after streaming 1020, $f_2^T$ corresponds to the component $1-\alpha_S$, which is reflected back toward the source voxel 1002 by the target voxel 1004; $f_1^T$ corresponds to the component $\alpha_S$, which is transmitted through the target voxel 1004 and onto another, adjacent voxel.

In an example in which the target voxel 1004 is complete pore space, all of the fluid flow provided to the target voxel 1004 (e.g., $f_1^S$) is transmitted through the target voxel 1004, and thus $\alpha_S=1$ and the reflected component $(1-\alpha_S)$ is thus 0. In this example, the FBP associated with the target voxel 1004 is 100.

In an example in which the target voxel 1004 is complete solid space, all of the fluid flow provided to the target voxel 1004 (e.g., $f_1^S$) is reflected back toward the source voxel 1002 by the target voxel 1004, and thus $\alpha_S=0$ and the reflected component $(1-\alpha_S)$ is thus 1. In this example, the FBP associated with the target voxel 1004 is 0.

In other examples in which the target voxel 1004 is partial solid/pore space, the FBP varies as a function of the amount of provided fluid ($f_1^S$) that is reflected back or transmitted by the target voxel 1004. As described further below, the FBP for a given voxel may be determined based on its permeability, or another material property, which are determined as described above.

Figure 11A:
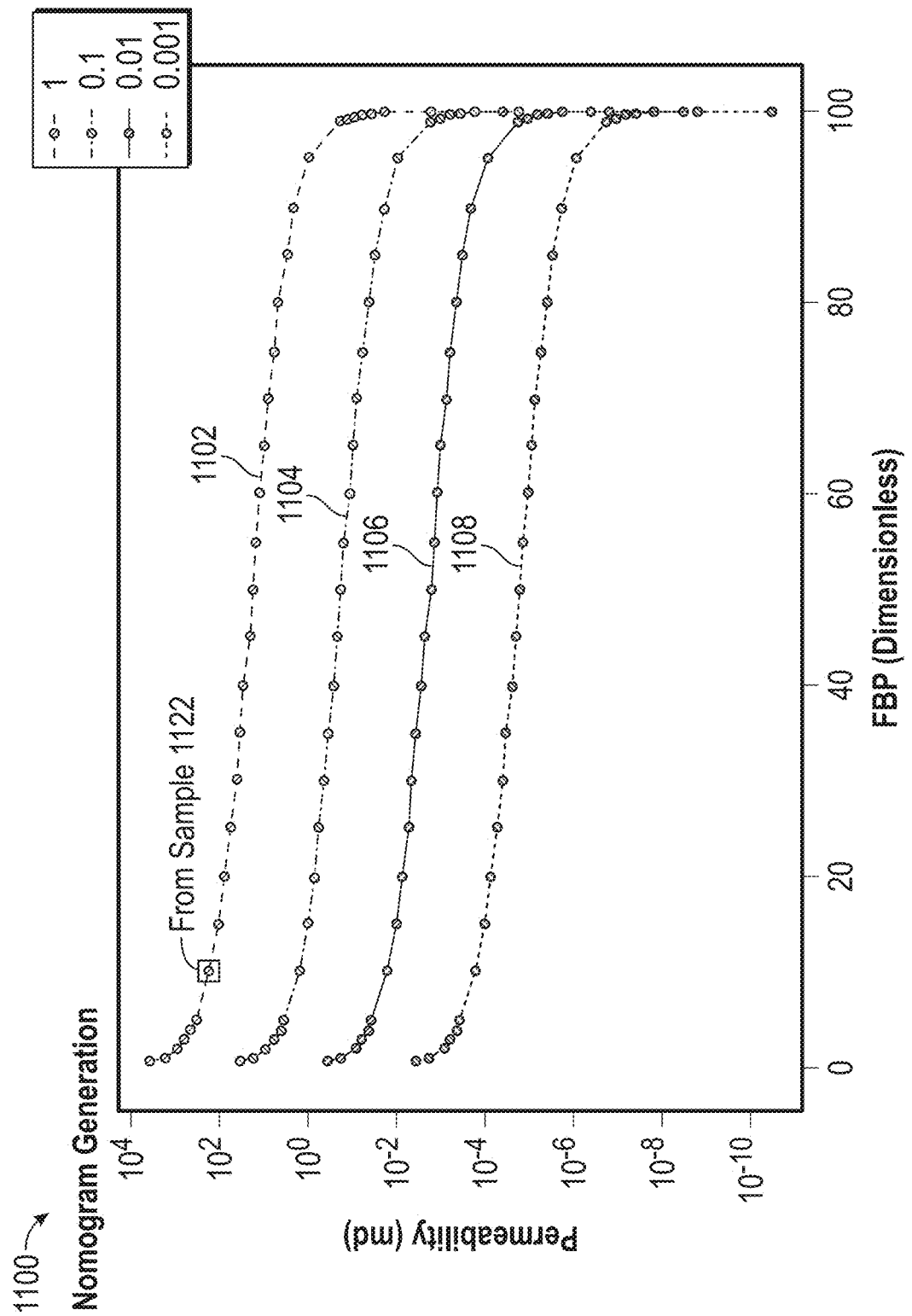
FIGS. 11a-11d show sets of nomograms that relate values of a material property of a rock sample, FBP values, and different grid sizes in accordance with principles disclosed herein.

FIG. 11a shows a set of nomograms 1100 that associates permeability values with FBP values for various grid sizes. In this context, grid size refers to or is related to voxel size/segmentation volume size. For example, a grid size of one micron means that each gridpoint (e.g., described with respect to FIG. 10) is specified to have a one micron spacing relative to other gridpoints. In this example, the set of nomograms 1100 includes a first nomogram 1102 for an exemplary grid size of 1 micron, a second nomogram 1104 for an exemplary grid size of 0.1 micron, a third nomogram 1106 for an exemplary grid size of 0.01 micron, and a fourth nomogram 1108 for an exemplary grid size of 0.001 micron. Although not depicted in FIG. 11, in some examples, one or more extrapolated nomograms are also included, which is not necessarily part of the original set of nomograms 1100 but rather is derived from the nomograms 1102, 1104, 1106, 1108 that are part of the set of nomograms 1100. The generation of the set of nomograms 1100 is described further below, with reference to FIG. 11b.

Figure 11B:
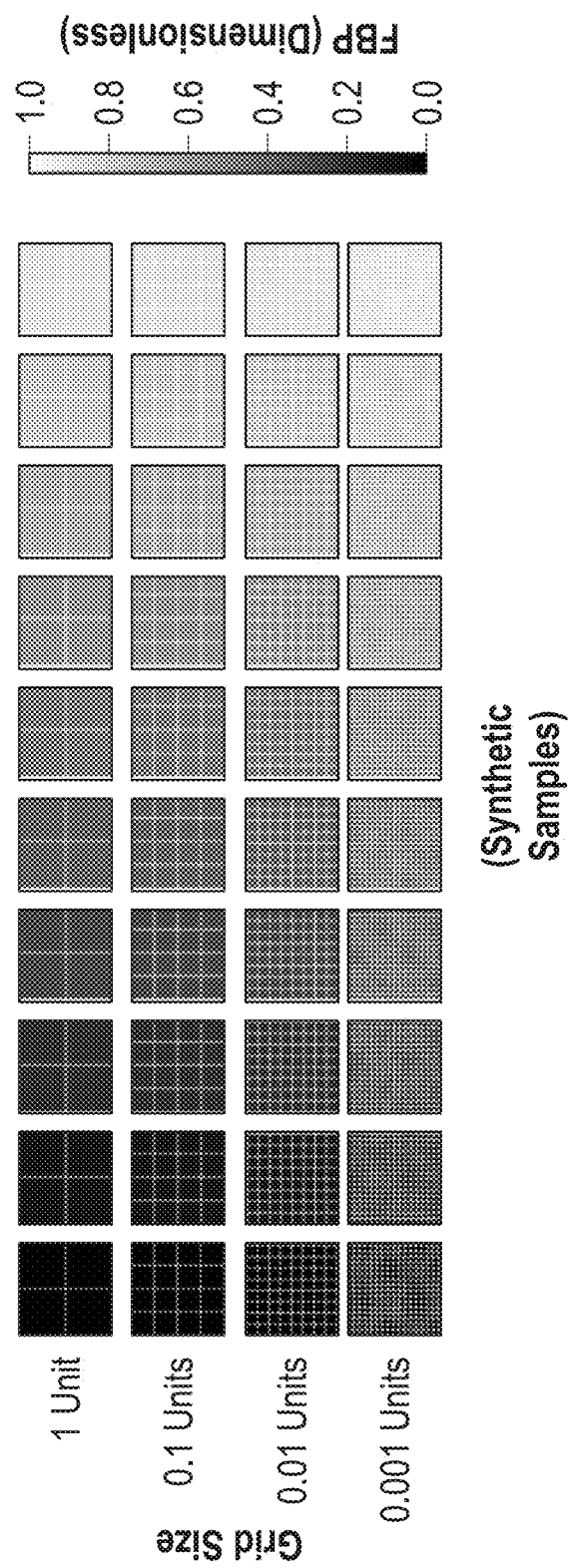

FIG. 11b shows an example set of synthetic samples 1120 used to generate the set of nomograms 1100 described above. For each grid size, multiple synthetic samples are created, each having a different assigned FBP. A permeability (or other material property) value is calculated for one grid square of a particular synthetic sample, and a nomogram is generated based on the resulting relationship between the grid size for a synthetic sample, the FBP for that synthetic sample, and the calculated permeability for one grid square of that synthetic sample.

For example, a synthetic sample 1122 is created for a grid size of 1 unit (e.g., micron) and having an FBP of approximately 10 (for an FBP scale of 0 to 100). A permeability value of one grid square of the synthetic sample 1122 is calculated to be approximately 100 millidarcy (md), which is plotted as a point in the nomogram 1102 in FIG. 11a as shown. Similarly, synthetic samples having different FBPs are created for the grid size of 1 unit, and permeability (or other material property) values are calculated for the grid squares of those synthetic samples that, when plotted, result in the nomogram 1102 in FIG. 11a. Creating synthetic samples at multiple grid sizes, across a range of FBPs, and calculating permeability (or other material property) values associated with a grid square of each synthetic sample thus results in the set of nomograms 1100 described above.

Figure 11C:
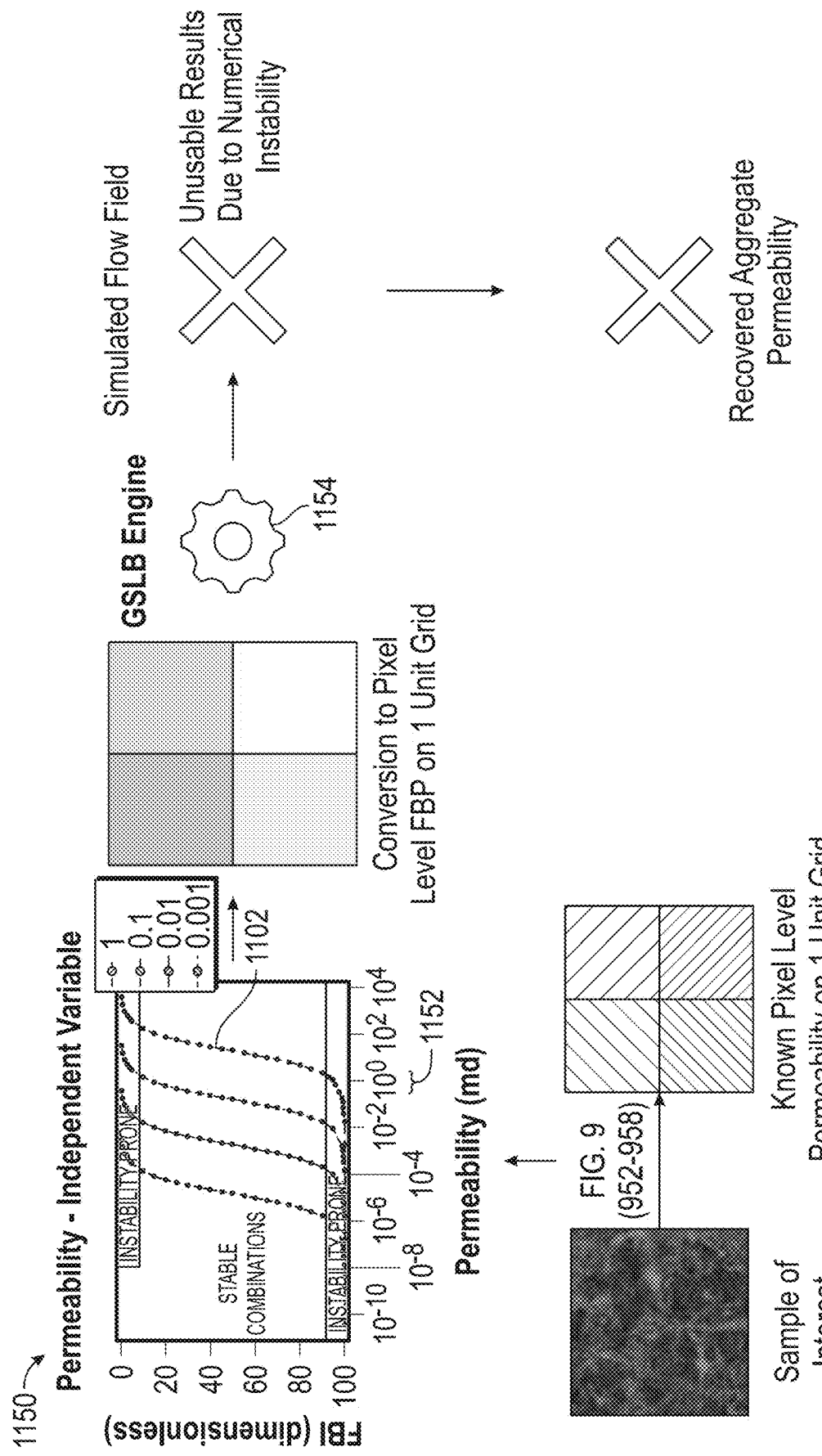

In these examples, each of the set of nomograms 1100 associates permeability values (e.g., determined as described above) with corresponding FBP values. For purposes of illustration, it is assumed that the previous blocks in FIG. 9 identify four rock fabrics that have different permeability values. FIG. 11c shows the set of nomograms 1100 as a set of nomograms 1150, in which the x-axis and the y-axis are reversed, so that permeability is the independent variable in the set of nomograms 1150. The four rock fabrics correspond to permeability values as shown at 1152. In some examples, FBP values in certain ranges at the end of the FBP scale (e.g., <10 and >90 for an FBP scale of 0 to 100) result in numerical instability during subsequent modeling, such as using a GSLB algorithm described further below. In FIG. 11c, the nomogram 1102 corresponding to a grid size of 1 unit (e.g., micron) is selected, which results in FBP values greater than 90 that correspond to the permeability values 1152 for the four rock fabrics. As a result, if nomogram 1102 is selected to generate the input to a GSLB engine 1154, the results or output of the GSLB engine 1154 may be unusable due to the numerical instability that results when the FBP values are in ranges that are instability-prone.

However, as demonstrated in FIG. 11c, the permeability values for the four rock fabrics could intersect more than one nomogram. As described above, it may be advantageous to avoid nomograms for which the permeability values of the rock fabrics are associated with FBP values in ranges that would result in numerical instability.

Figure 11D:
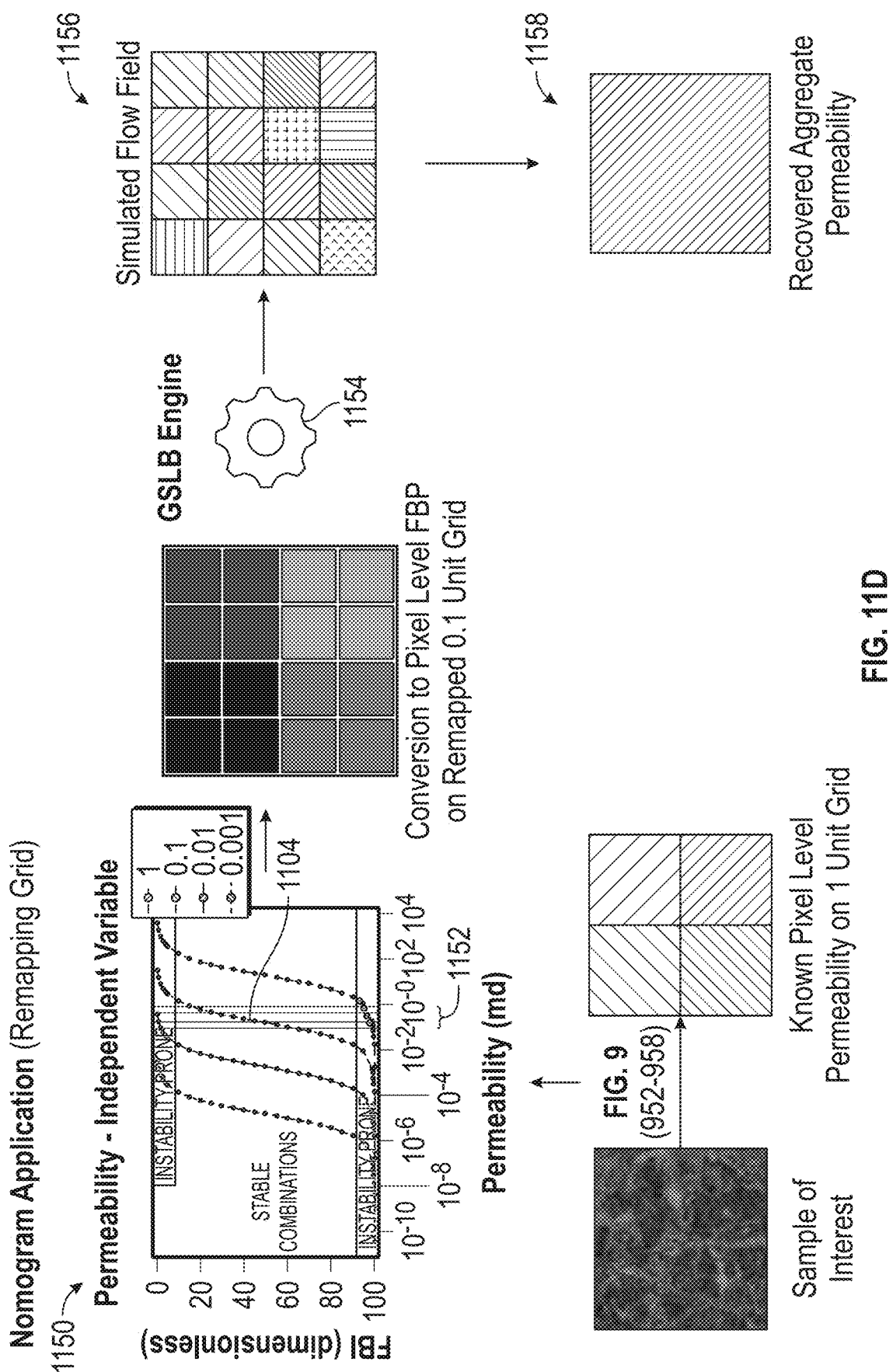

Thus, in examples of this description, a nomogram is selected that associates the material property (e.g., permeability in this example) of each of the four rock fabrics with an FBP value in a given range (e.g., greater than a lower FBP threshold (e.g., 10 for a scale of 0 to 100) and less than an upper FBP threshold (e.g., 90 for a scale of 0 to 100). Although not shown in the sets of nomograms 1100, 1150, in some cases, the set of nomograms 1100 does not initially include a nomogram that satisfies the FBP range constraints, and thus an extrapolated nomogram is constructed based on the other nomograms in the set of nomograms 1100. Regardless, FIG. 11d shows the set of nomograms 1150 in which the nomogram 1104 corresponding to a grid size of 0.1 unit (e.g., micron) is selected. Accordingly, the permeability values 1152 for the four rock fabrics results in FBP values between 10 and 90 as shown. As a result, selecting nomogram 1104 to generate the input to the GSLB engine 1154 for the permeability values 1152 enables the GSLB engine 1154 to provide a stable output, such as a simulated flow field 1156, which can then be mapped to a recovered aggregate permeability 1158 (e.g., a permeability tensor) associated with the initial rock sample.

Referring back to FIG. 9, the method 950 continues in block 962 with associating each voxel in the digital image volume (e.g., each determined fabric type) with the corresponding FBP value indicated by the selected nomogram (or an extrapolated nomogram), such as the nomogram 1104 in the example of FIG. 11d, described above.

Figure 12:
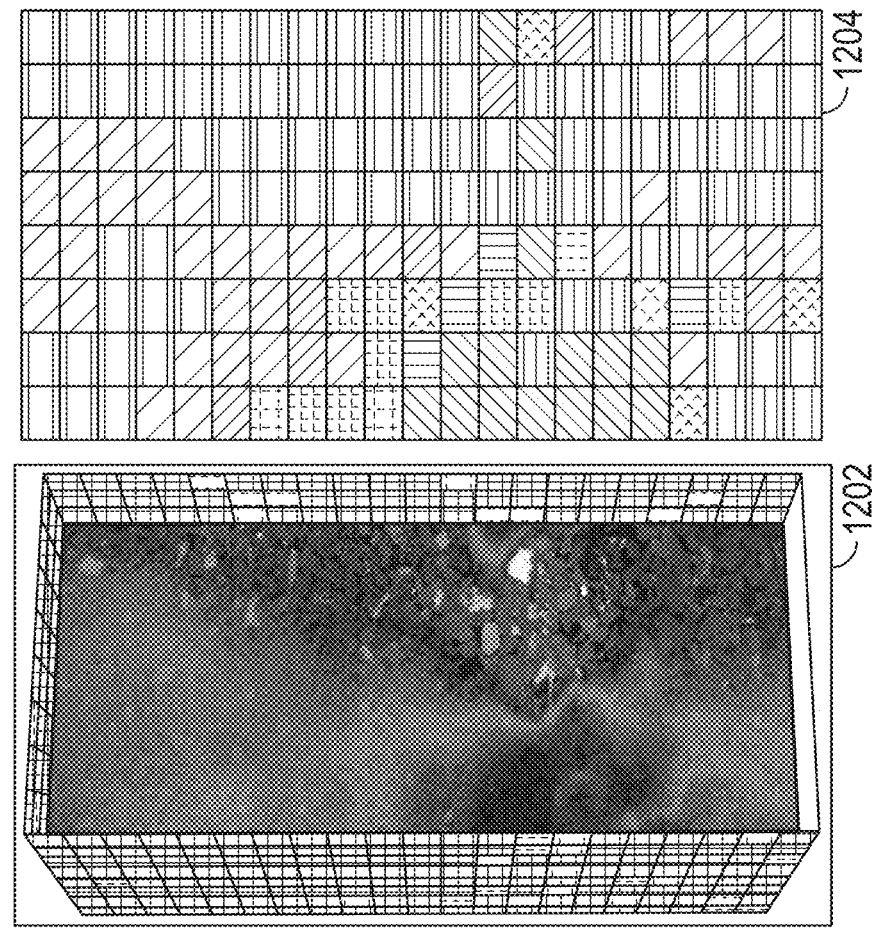
FIG. 12 shows an example of segmenting an image volume using the grid size of a nomogram selected from the set of nomograms in FIG. 11.

The method 950 then continues in block 964 with creating a 3D FBP volume having similar dimensions as the digital image volume. For example, FIG. 12 shows in 1202 an example digital image volume overlaid by a flow field derived from applying conventional LB to the full resolution digital image, and in 1204 an example flow field derived from applying GSLB to the corresponding coarsened digital image's 3D FBP volume. The voxel FBP values of the 3D FBP volume correspond to the grid size of the selected (or extrapolated) nomogram described above. For example, using the nomogram 1104 to determine FBP values for the permeability values 1152 of the four rock fabrics results in a grid size of 0.1 microns. As shown in FIG. 12, the resolution of the 3D FBP volume 1204 is coarser than that of the digital image volume 1202, however the specified grid size and FBP values input for the GSLB engine correspond to the selected nomogram 1104 (0.1 microns).

The method 950 then continues in block 966 with applying a GSLB algorithm to the 3D FBP volume 1204 created in block 964. The GSLB algorithm receives as input the FBP values determined in blocks 960 and 962, and described above with reference to FIGS. 11a-11d. Thereafter, mathematical operations particular to the GSLB algorithm, such as iterative streaming, collision and fractional-bounceback operations, are conducted on voxel locations in the 3D FBP volume 1204 until a stable flow velocity is computed for those voxel locations. These flow velocities, referred to in aggregate as the "flow field" can be used to compute a permeability tensor estimate for the digital image volume.

Figure 13:
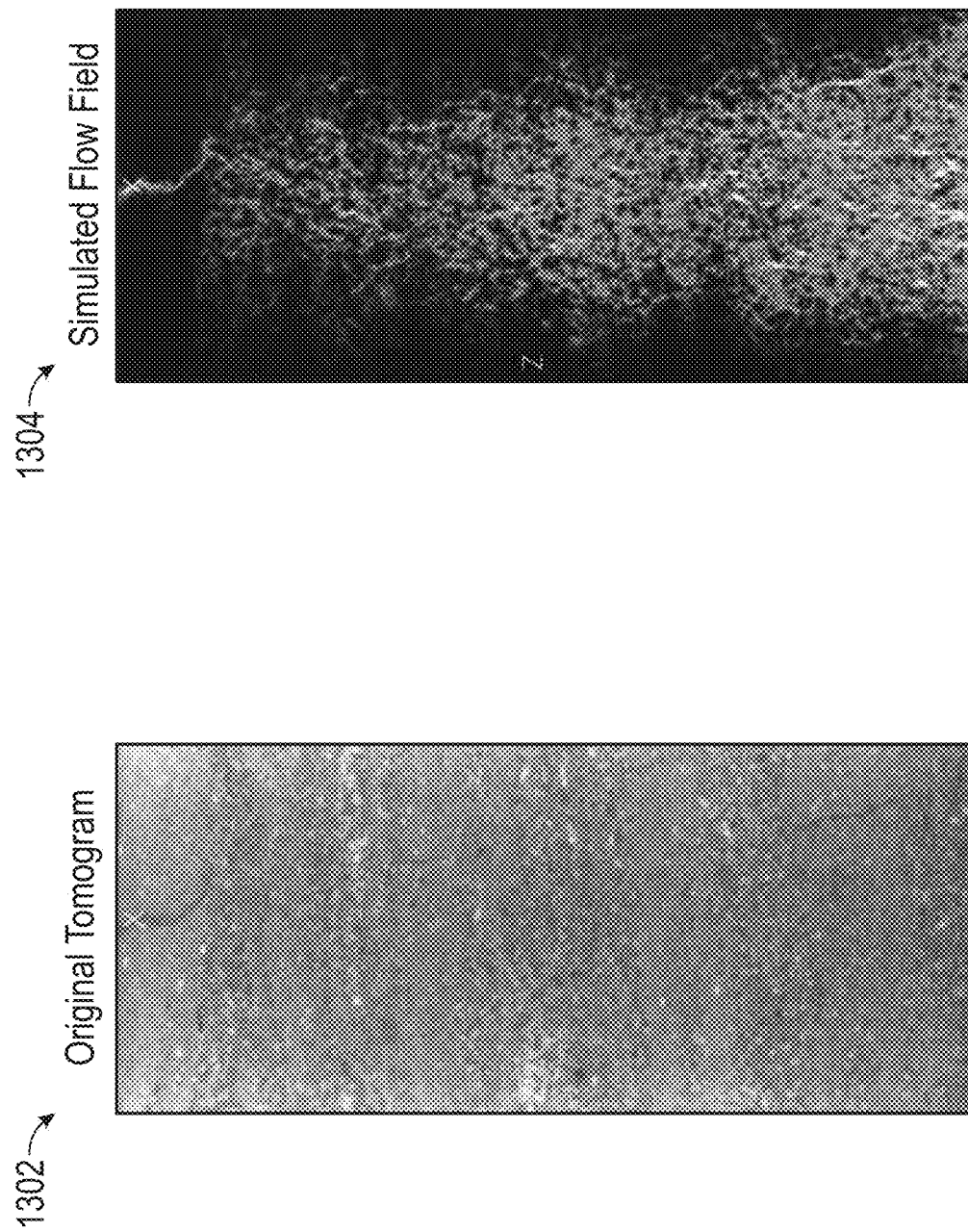
FIG. 13 shows a comparison of an original digital image and a simulated flow field in accordance with principles disclosed herein.

FIG. 13 shows a comparison between an original tomogram (e.g., a captured digital image) 1302 and a simulated flow field 1304 that results from, for example, applying the GSLB algorithm to the 3D FBP volume 1204.

Figure 14:
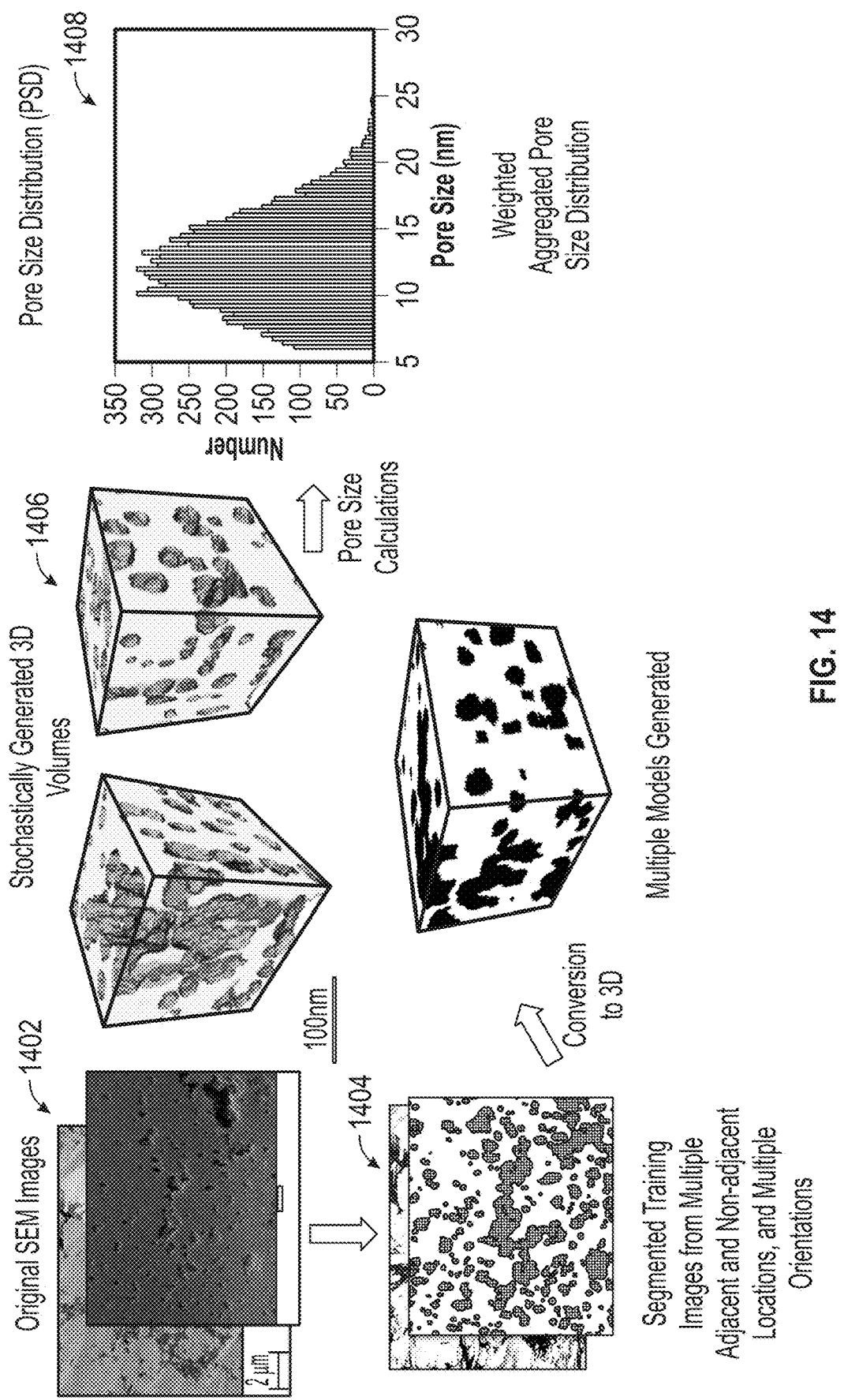
FIG. 14 shows a graphical flow chart of another method for analyzing rock samples in accordance with principles described herein.

FIG. 14 is a graphical flow chart of a method 1400 for analyzing a rock sample, such as the rock sample 104 described above. At 1402, SEM imaging is performed on a physical face or faces of the rock sample 104 as described above, which generates multiple 2D SEM images of the rock sample 104 (in some cases from different axial orientations as described above). The 2D SEM images at 1402 may be similar to the SEM images 500, 502, 510 described above with respect to FIGS. 5a-5c.

The method 1400 continues at 1404 where the SEM images from 1402 are optionally segmented, such as described above with respect to FIGS. 6a and 6b. By segmenting the SEM images obtained at 1402, fabrics of the larger rock sample 104 are captured at a fine level of granularity in two dimensions, which may then be leveraged to create a 3D digital model volume that represents the rock sample 104. In particular, the segmented 2D SEM image(s)

at 1404 may be used as training image(s) for a 2D-to-3D volume transformation. The 2D SEM images from 1402, as well as the segmented training images from 1404, may be from multiple adjacent and/or non-adjacent views of the rock sample 104.

The method 1400 continues at 1406, in which a cross-correlation function is applied to at least first and second 2D SEM images from 1402 to generate a 3D digital model volume. For example, one or more stochastic algorithms (e.g., a cross-correlation function) are applied to the 2D SEM images from 1402 (or segmented versions from 1404) to generate one of multiple realizations of statistically-similar or statistically-equivalent 3D pore-organic matrix volumes. In the example of the cross-correlation function, this process uses structural information (e.g., data indicative of correlation between different parts of the image) in the 2D training images (e.g., the 2D SEM image from 1402 or segmented version from 1404) to first break up the images into smaller constituent areas and then recombine those areas in a stochastic manner to synthetically generate statistically similar, but non-identical, versions of the original 2D training image. Subsequently, the original 2D training image, as well as its statistically similar versions, are projected into one or more imaginary planes (e.g., in 3D). These 3D projections, or "digital model volumes," may be used to statistically condition a subsequent iteration of generating synthetic, statistically similar images. In one example, such a conditioning process is useful to iteratively generate synthetic images that may be overlain or underlain with previously generated synthetic images in a manner that appears to more accurately reflect a natural look and/or structural continuity of a real-world rock sample.

The method 1400 continues at 1408, with determining a probability distribution of a pore size (e.g., a pore size distribution) of one of the 3D digital model volumes from 1406. In an example, the pore size distribution is determined based on image intensity values of pixels in the 2D SEM images from 1402 that were used to generate the 3D digital model volume used to determine the pore size distribution at 1408.

In some examples, determining the pore size distribution includes a numerical simulation using algorithms from exemplary direct numerical simulation techniques. For example, a two-phase lattice Boltzmann simulation may be utilized to estimate a numeric permeability based on the 3D digital model volume(s) for a given fabric type, while an object partitioning and point counting algorithm may be utilized to estimate a numeric pore size distribution based on the 3D digital model volume(s) for a given fabric type.

In the method 1400, aggregating information from multiple 2D SEM images (from 1402) or, optionally, segmented training images (from 1404) results in 3D digital model volume(s) at 1406 that more closely represent the features of the original rock sample 104. Additionally, in some examples, multiple 3D model volumes are used to determine correspondingly multiple pore size distributions at 1408. For example, the 3D digital model volumes are used as a modeling grid for one type of rock fabric (e.g., N realizations of one fabric type) to determine the desired material property or properties for that fabric type. Because the 3D model volumes represent N realizations for one fabric type, the resulting multiple pore size distributions at 1408 may also be aggregated, resulting in a final aggregate pore size distribution for that fabric type that has an improved accuracy (e.g., relative to a pore size distribution from only one 3D model volume realization).

In another example, because the 3D model volumes represent N realization for one fabric type, the 2D SEM images (from 1402) and/or the segmented training images (from 1404) may be generated from different rock samples 104, including from different geographic regions, provided that the different rock samples 104 include the same one fabric type being represented by the 3D model volumes. For example, a first 2D SEM image is of a first rock sample from a first geographic region, while another 2D SEM image is of a second rock sample from a second geographic region. It should be understood that geographic regions need not be separated by large distances, but rather may refer simply to different locations near an exploratory wellsite. However, the geographic regions may also be separated by large distances, provided that each of the different rock samples 104 includes the type of rock fabric represented by the 3D digital model volumes generated at 1406.

The above discussion is meant to be illustrative of various principles and embodiments of the present disclosure. While certain embodiments have been shown and described, modifications thereof can be made by one skilled in the art without departing from the spirit and teachings of the disclosure. The embodiments described herein are exemplary only, and are not limiting. Accordingly, the scope of protection is not limited by the description set out above, but is only limited by the claims which follow, that scope including all equivalents of the subject matter of the claims.

What is claimed is:

1. A method for analyzing a rock sample, comprising:
   performing scanning electron microscope (SEM) imaging of a plurality of physical faces of a rock sample to generate two-dimensional (2D) SEM images of the physical faces;
   applying a cross-correlation function to a first 2D SEM image and a second 2D SEM image to generate a three-dimensional (3D) digital model volume based on the first and second 2D SEM images; and
   determining a probability distribution of a pore size of the 3D digital model volume based on an image intensity value of a pixel in each of the first and second 2D SEM images.

2. The method of claim 1, wherein a resolution of the 3D digital model volume is finer than a resolution of the digital image volume.

3. The method of claim 1, wherein an axial orientation of the first SEM image is different than an axial orientation of the second 2D SEM image.

4. The method of claim 1, wherein the rock sample is a first rock sample from a first geographic region, the method further comprising:
   performing SEM imaging of a plurality of physical faces of a second rock sample from a second geographic region;
   applying the cross-correlation function to the first 2D SEM image and third 2D SEM image to generate a second 3D digital model volume, wherein the third 2D SEM image is of the second rock sample;
   wherein a type of rock fabric represented by the 3D digital model volume is present in each of the first and third 2D SEM images.

5. The method of claim 1, further comprising:
   applying the cross-correlation function to a plurality of the 2D SEM images to generate a plurality of 3D digital model volumes for each of the plurality of rock fabrics; and
   performing direct numerical simulations using the plurality of 3D digital model volumes as a modeling grid for one of the rock fabrics to determine the probability distribution of the pore size for the one of the rock fabrics.

6. The method of claim 5, further comprising:
aggregating the plurality of 3D digital model volumes for one of the rock fabrics to produce an aggregated result; and
updating the determination of the probability distribution of the pore size for the one of the rock fabrics responsive to the aggregated result.

7. A system for analyzing a rock sample, comprising:
a scanning electron microscope (SEM) configured to generate two-dimensional (2D) SEM images of physical faces of a rock sample; and
a computing device coupled to the SEM and comprising:
a processor; and
a memory coupled to the processor and configured to store instructions that, when executed by the processor, configure the computing device to:
apply a cross-correlation function to a first 2D SEM image and a second 2D SEM image to generate a three-dimensional (3D) digital model volume based on the first and second 2D SEM images; and
determine a probability distribution of a pore size of the 3D digital model volume based on an image intensity value of a pixel in each of the first and second 2D SEM images.

8. The system of claim 7, wherein a resolution of the 3D digital model volume is finer than a resolution of the digital image volume.

9. The system of claim 7, wherein an axial orientation of the first SEM image is different than an axial orientation of the second 2D SEM image.

10. The system of claim 7, wherein the rock sample is a first rock sample from a first geographic region, and wherein the instructions, when executed by the processor, configure the computing device to:
receive SEM imaging of a plurality of physical faces of a second rock sample from a second geographic region;
apply the cross-correlation function to the first 2D SEM image and third 2D SEM image to generate a second 3D digital model volume, wherein the third 2D SEM image is of the second rock sample;
wherein a type of rock fabric represented by the 3D digital model volume is present in each of the first and third 2D SEM images.

11. The system of claim 7, wherein the instructions, when executed by the processor, configure the computing device to:
apply the cross-correlation function to a plurality of the 2D SEM images to generate a plurality of 3D digital mod& volumes for each of the plurality of rock fabrics; and
perform direct numerical simulations using the plurality of 3D digital mod& volumes as a modeling grid for one of the rock fabrics to determine the probability distribution of the pore size for the one of the rock fabrics.

12. The system of claim 11, wherein the instructions, when executed by the processor, configure the computing device to:

aggregate the plurality of 3D digital model volumes for one of the rock fabrics to produce an aggregated result; and
update the determination of the probability distribution of the pore size for the one of the rock fabrics responsive to the aggregated result.

13. A non-transitory, computer-readable medium encoded with instructions that, when executed by a processor, cause the processor to:
receive two-dimensional (2D) scanning electron microscope (SEM) images of physical faces of a rock sample;
apply a cross-correlation function to a first 2D SEM image and a second 2D SEM image to generate a three-dimensional (3D) digital model volume based on the first and second 2D SEM images; and
determine a probability distribution of a pore size of the 3D digital model volume based on an image intensity value of a pixel in each of the first and second 2D SEM images.

14. The non-transitory, computer-readable medium of claim 13, wherein a resolution of the 3D digital model volume is finer than a resolution of the digital image volume.

15. The non-transitory, computer-readable medium of claim 13, wherein an axial orientation of the first SEM image is different than an axial orientation of the second 2D SEM image.

16. The non-transitory, computer-readable medium of claim 13, wherein the rock sample is a first rock sample from a first geographic region, and wherein the instructions, when executed by the processor, cause the processor to:
receive SEM imaging of a plurality of physical faces of a second rock sample from a second geographic region;
apply the cross-correlation function to the first 2D SEM image and third 2D SEM image to generate a second 3D digital model volume, wherein the third 2D SEM image is of the second rock sample;
wherein a type of rock fabric represented by the 3D digital model volume is present in each of the first and third 2D SEM images.

17. The non-transitory, computer-readable medium of claim 13, wherein the instructions, when executed by the processor, cause the processor to:
apply the cross-correlation function to a plurality of the 2D SEM images to generate a plurality of 3D digital model volumes for each of the plurality of rock fabrics; and
perform direct numerical simulations using the plurality of 3D digital model volumes as a modeling grid for one of the rock fabrics to determine the probability distribution of the pore size for the one of the rock fabrics.

18. The non-transitory, computer-readable medium of claim 17, wherein the instructions, when executed by the processor, cause the processor device to:
aggregate the plurality of 3D digital model volumes for one of the rock fabrics to produce an aggregated result; and
update the determination of the probability distribution of the pore size for the one of the rock fabrics responsive to the aggregated result.

* * * * *